US007442545B2

(12) United States Patent
Reynolds et al.

(10) Patent No.: US 7,442,545 B2
(45) Date of Patent: Oct. 28, 2008

(54) NEURAL COLONY FORMING ASSAY

(75) Inventors: Brent A. Reynolds, Brisbane (AU); Sharon A. Louis, Vancouver (CA)

(73) Assignee: Stemcell Technologies, Inc., Vancouver, British Columbia (CA)

( * ) Notice: Subject to any disclaimer, the term of this patent is extended or adjusted under 35 U.S.C. 154(b) by 467 days.

(21) Appl. No.: 10/938,579

(22) Filed: Sep. 13, 2004

(65) Prior Publication Data

US 2005/0112546 A1 May 26, 2005

Related U.S. Application Data

(60) Provisional application No. 60/577,599, filed on Jun. 8, 2004, provisional application No. 60/558,985, filed on Apr. 5, 2004, provisional application No. 60/545,281, filed on Feb. 18, 2004, provisional application No. 60/509,257, filed on Oct. 8, 2003, provisional application No. 60/502,256, filed on Sep. 12, 2003.

(51) Int. Cl.
*C12N 5/00* (2006.01)
*C12N 5/06* (2006.01)
*C12N 5/08* (2006.01)

(52) U.S. Cl. .................. 435/325; 435/368; 435/354; 435/365; 435/377

(58) Field of Classification Search ........................ None
See application file for complete search history.

(56) References Cited

U.S. PATENT DOCUMENTS

| 5,750,376 | A | | 5/1998 | Weiss et al. | |
|---|---|---|---|---|---|
| 5,817,622 | A | * | 10/1998 | Johnson et al. | 514/2 |
| 5,851,832 | A | | 12/1998 | Weiss et al. | |
| 5,968,829 | A | * | 10/1999 | Carpenter | 435/467 |
| 5,980,885 | A | | 11/1999 | Weiss | |
| 5,981,165 | A | | 11/1999 | Weiss | |
| 6,093,531 | A | | 7/2000 | Bjornson et al. | |
| 6,103,530 | A | | 8/2000 | Carpenter | |
| 6,165,783 | A | | 12/2000 | Weiss | |
| 6,238,922 | B1 | * | 5/2001 | Uchida | 435/380 |
| 6,638,763 | B1 | * | 10/2003 | Steindler et al. | 435/368 |
| 2002/0164791 | A1 | * | 11/2002 | Van Der Kooy et al. | 435/366 |

FOREIGN PATENT DOCUMENTS

| CA | 2148138 | 1/2002 |
|---|---|---|
| CA | 2147162 | 4/2002 |
| CA | 2113118 | 9/2002 |
| WO | WO/9830678 | 7/1998 |
| WO | WO/02090511 | 11/2002 |

OTHER PUBLICATIONS

On-line Medical Dictionary definition for "cytokine"; http://cancerweb.ncl.ac.uk/cgi-bin/omd?cytokine, accessed Feb. 7, 2007.*
Sargent-Welch catalog; pages for 24-well and 35 mm culture dishes, downloaded from www.sargentwelch.com on Nov. 21, 2007.*
Chen, SS. et al., "Multiliniage Differention of Rhesus Monkey Embryonic Stem Cells in Three-Dimensional Culture Systems", Stem Cells, May 2003, pp. 281-295, vol. 21, Alphamed Press.
O'Connor, SM. et al., "Survival and neurite outgrowth of rat cortical neurons in three-dimensional agarose and collagen gel matrices", Neuroscience Letters, May 25, 2001, vol. 304(3), pp. 189-193.
O'Shaughnessy, TJ. eta l., "Functional synapse formation among rat cortical neurons grown on three-dimensional collagen gels", Neuroscience Letters, Apr. 17, 2003, vol. 340(3), pp. 169-172.
Reynolds, BA., et al., "Clonal and population analyses demonstrate that an EGF-responsive mammalian embryonic CNA precursor is a stem cell", Developmental Biology, Apr. 10, 1996, vol. 175(1), pp. 1-13, Academic Press Inc.
Schafer, KH. et al., "Differentiation of neurospheres from the enteric nervous system", Pediactric Surgery International, Jul. 5, 2003, vol. 19(5), pp. 340-344.
Shetty, AK., "Progenitor cells from the CA3 region of the embryonic day 19 rat hippocampus generate region-specific neuronal phenotypes in vitro", Hippocampus, Mar. 10, 2004, vol. 14(5), pp. 595-614, Wiley Interscience.
Ahmed, et al. "BDNF enhances the differentiation but not the survival of CNS stem cell-derived neuronal precursors", Journal of Neuroscience, Aug. 1995, vol. 15(8), pp. 5765-5778.
Au, et al. "Culturing olfactory ensheathing glia from the mouse olfactory epithelium", Methods in Molecular Biology, 2002, vol. 198, pp. 49-54.
Barnet, et al. "Olfactory ensheathing cells" Methods in Molecular Biology, 2002, vol. 198, pp. 41-48.
Bjornson, et al. "Turning brain into blood: A hematopoietic fate adopted by adult neural stem cells in vivo", Science, Jan. 22, 1999, vol. 283(5401), pp. 534-537.
Blackshaw, et al. "Stem Cells that know their place", Nature Neuroscience, Dec. 2002, vol. 5(12), pp. 1251-1252.
Caldwell, et al. "Growth factors regulate the survival and fate of cells derived from human neurospheres", Nature Biotechnology, May 2001, vol. 19(5), pp. 475-479.

(Continued)

*Primary Examiner*—David Romeo
*Assistant Examiner*—Daniel C Gamett
(74) *Attorney, Agent, or Firm*—Kramer & Amado PC

(57) ABSTRACT

A neural colony forming cell (NCFC) assay is described. The assay allows one to distinguish neural stem cells from neural progenitor cells. In one embodiment, the present invention provides a method for identifying neural stem cells or neural progenitor cells comprising: (a) suspending neural cells in a semi-solid medium which supports the growth of neural cells; (b) plating the cells in the semi-solid medium at a density that allows for the production of colonies; (c) culturing the plated cells until size differences can be discerned between the colonies; and (d) estimating colony size wherein the larger colonies are likely produced by neural stem cells and wherein the small colonies are likely produced by neural progenitor cells In alternate embodiments, NSC can be distinguished from neural progenitor cells by determining the morphology or antigen expression of the colonies.

14 Claims, 29 Drawing Sheets

OTHER PUBLICATIONS

Craig, et al. "In vivo growth factor expansion of endogenous subependymal neural precursor cell populations in the adult mouse brain", Journal of Neuroscience, Apr. 15, 1996, vol. 16(8), pp. 2649-2658.

Engstrom, et al. "A method for clonal analysis of epidermal growth factor-responsive neural progenitors", Journal of Neuroscience Methods, Jun. 30, 2002, vol. 117(2), pp. 111-121.

Gage, et al. "Isolation, characterization, and use of stem cells from the CNS", Annual Review of Neuroscience, 1995, vol. 18, pp. 159-192.

Galli, et al. "Neural stem cells: An overview", Circ. Res., 2003, vol. 92, pp. 598-608.

Gritti, et al. "Cultures of stem cells of the central nervous system", In Protocols for Neural Cell Culture, 2001, 3rd edition, Federoff & Richardson, Human Press Inc., pp. 173-197.

Horrocks et al. "Formation of neurospheres from human embryonal carcinoma cells", Biochem Biophys Res Commun, May 2003, vol. 304(2), p. 411.

Hulspas et al. "Characterization of neurosphere cell phenotypes by flow cytometry", Cytometry, Jul. 1, 2000, vol. 40(3), pp. 245-250.

Kanemura, et al. "Evaluation of in vitro proliferative activity of human fetal neural stem/progenitor cells using indirect measurements of viable cells based on cellular metabolic activity", Journal Neurosci Res, Sep. 15, 2002, vol. 69(6), pp. 869-879.

Kim, et al. "A FACS side population analysis separates distinct populations of neural stem versus progenitor cells from adult and embryonic forebrains", Soc for Neurosci abstract, 2001.

Krewson, et al. "Cell aggregation and neurite outgrowth in gels of extracellular cells" J Med, 1994, vol. 20 (3-4), pp. 555-562.

Kukekov et al. "Multipotent stem/progenitor cells with similar properties arise from two neurogenic regions of adult human brain", Exp Neurol, 1999, vol. 156, pp. 333-344.

Lai, et al. "Sonic hedgehog regulates adult neural progenitor proliferation in vitro and in vivo", Nat Neurosci, Jan. 2003, vol. 6(1), p. 21.

Lanotte, et al. "Collagen gels as a matrix for haemopoiesis", J Cell Physiol, 1981, vol. 106, pp. 269-277.

Laywell, et al. "Multipotent neurospheres can be derived from forebrain subependymal zone and spinal cord of adult mice after protracted postmortem intervals" Exp. Neurobiol, 1999, vol. 156, pp. 430-433.

Laywell, et al. "Production and analysis of neurospheres from acutely dissociated and postmortem CNS specimens" Methods Mol Biol, 2002, vol. 198, pp. 15-27.

Le Belle, et al. "Stem cells for neurodegenerative disorders: Where can we go from here?" Biodrugs, 2002, vol. 16(6), pp. 389-401.

Lindvall, et al. "Brain repair by cell replacement and regeneration" PNAS, Jun. 24, 2003, vol. 100(13), pp. 7430-7431.

Lobo, et al. "Cellular characterization of epidermal growth factor-expanded free-floating neurospheres", J. Histochem Cytochem, Jan. 2003, vol. 51(1), pp. 89-103.

Low, et al. "Neural precursor cells form rudimentary tissue-like structures in a rotating-wall vessel bioreactor", In Vitro Cell Dev bio Anim, Mar. 2001, vol. 37(3), pp. 141-147.

Lowenberg, et al. "An assay for serum cytotoxicity against erythroid precursor cell in pure red cell aplasia", Biomed, Nov. 1977, vol. 27(8), pp. 285-289.

Mitchell, et al. "Matrix cells from Wharton's Jelly form neurons and glia" Stem Cells, 2003, vol. 21, pp. 50-60.

Morshead, et al. "Neural stem cells in the adult mammalian forebrain: a relatively quiescent subpopulation of subependymal cells", Neuron, Nov. 1994, vol. 13(5), pp. 1071-1082.

Nunes, et al. "Identification and isolation of multipotenital neural progenitor cells from the subcortical white matter of te adult human brain", Nat Med, Apr. 2003, vol. 9(4), pp. 439-447.

O'Connor, et al. "Primary neural precursor cell expansion, differentiation and cytosolic Ca2+ responsive in three-dimensional collagen gel", J. Neurosci Methods, 2000, vol. 102, pp. 187-195.

O'Connor, et al. "Isolation and propagation of stem cells from various regions of the embryonic mammalian central nervous system", In Cell Biology: A Laboratory Handbook, 2nd Ed., 1998, vol. 1, Academic Press, pp. 149-153.

Palmer, et al. "Fibroblast growth factor-2 activates a latent neurogenic program in neural stem cells from diverse regions of the adult CNS", J Neurosci, Oct. 1, 1999, vol. 19(19), pp. 8487-8797.

Parmar et al. "Regional specification of neurosphere cultures derived from subregions of the embryonic telencephalon" Mol Cell Neurosci, Dec. 2002, 21(4), pp. 645-656.

Price, et al. "Neural Stem Cells", Curr Opin Neurobiol, Oct. 2001, vol. 11(5), pp. 564-567.

Represa, et al. "EGF-responsive neural stem cells are a transient population in the developing mouse spinal cord", Eur J Neurosci, 2001, vol. 14, pp. 452-462.

Reubinoff, et al. "Neural progenitors from human embryonic stem cells" Nat Biotech, Dec. 2001, vol. 19, p. 1134.

Reynolds, et al. "A multipotent EGF-responsive striatal embryonic progenitor cell produces neurons and astrocytes" J Neurosci, Nov. 1992, vol. 12(11), pp. 4565-4574.

Reynolds, et al. "Central nervous system growth and differentiation factors: clinical horizons—truth or dare?", Curr Opin Biotech, Dec. 1993, vol. 4(6), pp. 734-738.

Ingram et al., "Identification of a novel hierarchy of endothelial progenitor cells utilizing human peripheral and umbilical cord blood", Nov. 2004, vol. 104(9), pp. 2752-2760.

Reynolds, et al. "Generation of neurons and astrocytes from isolated cells of adult mammalian central nervous system" Science, Mar. 27, 1992, vol. 255 (5052), pp. 1707 to 1710.

Rietze, et al. "Purification of a pluripotent neural stem cell from the adult mouse brain", Nat, Aug. 16, 2001, vol. 412, pp. 736-739.

Suslov, et al. "Neural stem cell heterogeneity demonstrated by molecular phenotyping of clonal neurospheres", PNAS, Oct. 29, 2002, vol. 99(22), pp. 14506-14511.

Suslov, et al. "RT-PCR amplification of mRNA from single brain neurospheres", J Neurosci Meth, 2000, vol. 96, pp. 57-61.

Tropepe, et al. "Distinct neural stem cells proliferate in response to EGF and FGF in the developing mouse telencephalon" Dev Biol, 1999, vol. 208, pp. 166-188.

Uchida, et al. "Direct Isolation of human central nervous system stem cells", PNAS, Dec. 2000, vol. 97(26), pp. 14720-14725.

Vescovi, et al. "bFGF regulates the proliferative fate of unipotent (neuronal) and bipotent (neuronal/astroglial) EGF-generated CNS progenitor cells", Neuron, Nov. 1993, vol. 11(5), pp. 951-966.

Vescovi, et al. "Clonal analyses of cryopreservation of neural stem cell cultures", Methods Mol Biol, 2002, vol. 198, pp. 115-123.

Vescovi, et al. "Isolation and cloning of multipotential stem cells from the embryonic human CNS and establishment of transplantable human neural stem cell lines by epigenetic stimulation", Exp Neurol, 1999, vol. 156,.pp. 71-83.

Wang et al. "Isolation, cultivation and identification of neural stem cell from human embryonic CNS", Sheng Wu Yi Xue Gong Cheng Xue Za Zhi, 2002, vol. 19(2), pp. 264-267.

Weiss et al. "Is there a neural stem cell in the mammalian forebrain?", Trends Neurosci, Sep. 1996, vol. 19(9), pp. 387-393.

Weiss, eta l. "Multipotent CNS stem cells are present in the adult mammalian spinal cord and ventricular neuroaxis", J. Neurosci, Dec. 1, 1996, vol. 16(23), pp. 7599-7609.

Whitehead, et al. "A method for the isolation and culture of human colonic crypts in collagen gels", In vitro Cell Dev Biol, 1987, vol. 23(6), pp. 436-442.

Wu, et al. "Isolation of Stem and precursor cells from fetal tissue", Methods Mol Bol, 2002, vol. 198, pp. 29-40.

Yang, et al. "Long-term culture and differentiation of neural stem cells of embryonic mice", Zhonghua Wai Ke Za Zhi, Oct. 2002, vol. 40(10), pp. 783-785.

Zhang, et al. "In vitro differentiation of transplantable neural precursors from human embryonic stem cells", Nat Biotech, Dec. 2001, vol. 19, p. 1129.

Zhou, et al. "Three to four-year-old nonpassaged EGF-responsive neural progenitor cells: Proliferation, apoptosis, and DNA repair", Exp. Neurol, 2000, vol. 164, pp. 200-208.

Brewer, et al. Primary rat brain cell culture from hibernate tissue (methods based on Brewer et al. (1993) J. Neurosci. Res. 35:567-576 and Brewer & Price (1996) Neuroreport 7: 1509-1512), Brain Bits Flyer.

Lin et al., "Nerual stem cell differentiation in a cell-collagen-bioreactor culture system", Developmental Brain Research, Nov. 25, 2004, vol. 153(2), pp. 163-173.

Lowenstein & Arsenault, "Dentate granule cell layer collagen explant cultures: spontaneous axonal growth and induction by brain-derived neurotrophic factor or basic fibroblast growth factor", Neuroscience, Oct. 1996, vol. 74(4), pp. 1197-1208.

Ma et. al., "CNS stem and progenitor cell differentiation into functional neuronal circuits in three-dimensional collagen gels", Experimental Neurology, Dec. 2004, vol. 190(2), pp. 276-288.

Morshead & van der Kooy, "Disguising adult neural stem cells", Current Opinion in Neurobiology, Feb. 2004, vol. 14(1), pp. 125-131.

O'Connor et al., "Primary neural precursor cell expansion, differentiation and cytosolic Ca2+ response in three-dimensional collagen gel", Oct. 30, 2000, vol. 102(2), pp. 187-195.

* cited by examiner

A: > 2mm
B: 1-2 mm
C: 0.5-1 mm
D: < 0.5 mm

Figure 13. Different colony morphologies observed for colonies > 2 mm in diameter Figure 14. Different colony morphologies observed for colonies 1 - 2 mm in diameter Figure 15. Different colony morphologies observed for colonies 0.5 - 1 mm in diameter Figure 16. Different colony morphologies observed for colonies < 0.5 mm in diameter

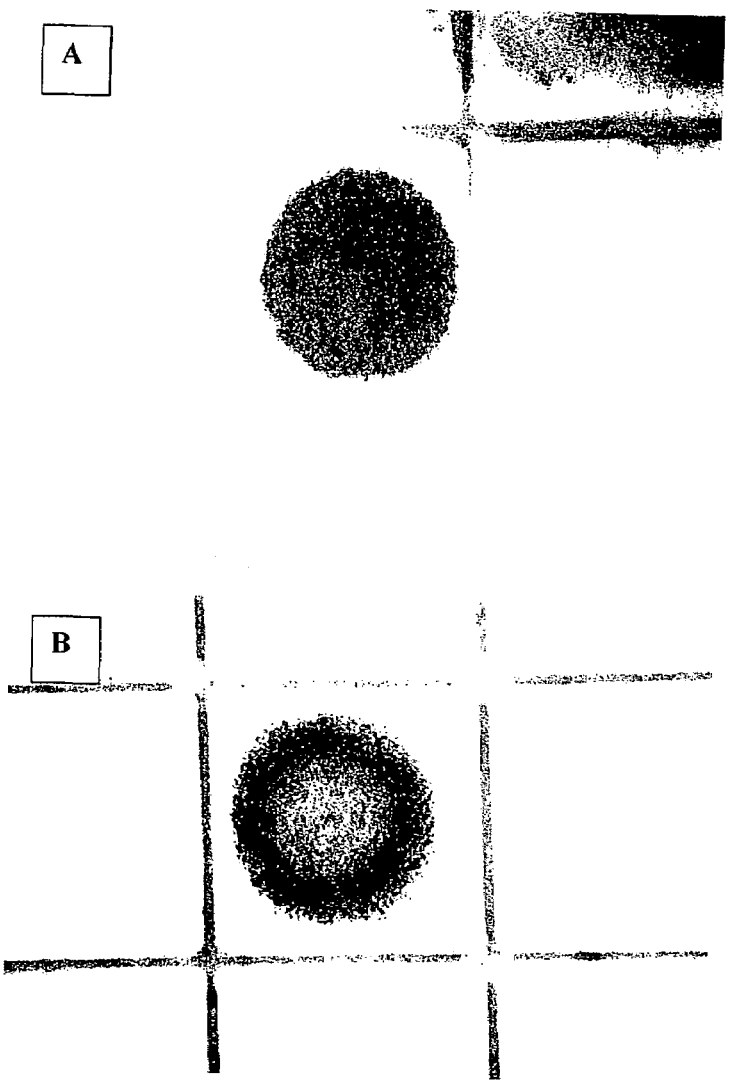
Figure 23. NCFC colonies from embryonic day 18 (E18) rat cortical cells. Two colonies 1 – 2 mm in diameter (A, B) generated by E18 rat cortical cells in the NCFC assay

NEURAL COLONY FORMING ASSAY

This application claims the benefit under 35 USC §119(e) from U.S. provisional patent applications Ser. No. 60/502,256 filed Sep. 12, 2003; Ser. No. 60/509,257 filed Oct. 8, 2003; Ser. No. 60/545,281 filed Feb. 18, 2004; Ser. No. 60/558,985 filed Apr. 5, 2004, and Ser. No. 60/577,599 filed Jun. 8, 2004, all of which are incorporated herein by reference in their entirety.

FIELD OF THE INVENTION

The present invention relates to a Neural Colony Forming Cell (NCFC) assay for the isolation, identification and discrimination of neural stem cells and neural progenitor cells.

BACKGROUND OF THE INVENTION

The development of the mammalian central nervous system (CNS) begins in the early stage of fetal development and continues until the post-natal period. In the adult CNS there are primarily three cells: neurons, astrocytes and oligodendrocytes. The first stage of neural development in the embryo is cell genesis, a period of precise temporal and spatial sequence in which proliferation by stem and progenitor cells give rise to the precursors that will differentiate into mature CNS cells. The second step is a period of cell differentiation and migration where neuroblasts (cells that will give rise to neurons) and glialblasts (cells that will give rise to astrocytes and oligodendrocytes) differentiate and migrate to their final positions. The third stage of development occurs when cells acquire specific mature phenotypic qualities such as neurons expressing particular neurotransmitters. The final stage of CNS development is a period of selective cell death, wherein the death and degeneration of specific cells, fibers and connections "fine-tune" the circuitry of the nervous system.

Unlike many other tissues of the body the mammalian CNS has traditionally exhibited little capacity to generate new cells in response to injury or disease. However, the relatively recent discovery of cells within the adult CNS that exhibit stem cell characteristics in vitro (Reynolds and Weiss, 1992) together with the re-examination (Altman, 1962; Altman and Das, 1965) of small proliferative zones in the adult brain (Alvarez-Buylla et. al., 2001) have led to the belief that the adult mammalian CNS retains the ability to generate new cells and that neural stem cells are the source of the proliferating precursors.

Within the CNS, neural stem cells (NSC) can be differentiated from progenitor cells primarily on their proliferative and differentiation potential. Based on the Potten and Loeffler (Potten and Loeffler, 1990) definition, NSC can be differentiated from progenitor cells by their ability to exhibit self-maintenance, produce a large number of progeny and to produce mature cells of all three primary cells types in neural tissue.

The critical identifying feature of a stem cell is its ability to exhibit self-renewal or to generate more of itself. In its simplest definition a stem cell would be a cell with the capacity for self-maintenance. However, this definition can be problematic as a large number of cells may be considered to fulfill this criteria. A more stringent and practical definition of a stem cell, is provided by Potten and Loeffler (1990) who have defined stem cells as "undifferentiated cells capable of a) proliferation, b) self-maintenance, c) the production of a large number of differentiated functional progeny, d) regenerating the tissue after injury, and e) a flexibility in the use of these options."

Culture systems have proven to be invaluable tools in studying and understanding the cellular and molecular properties of biological processes and systems. With respect to neural stem cells, a tissue culture method has been developed that allows the isolation, proliferation and expansion of neural stem cells and the subsequent differentiation of their progeny into the three primary cells types of the CNS (Reynolds and Weiss, 1996). Reynolds and Weiss identified a neural stem cell based on functional criteria. These criteria include the ability to 1) proliferate and generate a large number of progeny, 2) self-renew over an extended period of time in long-term cultures, and 3) continue to give rise to the primary cell types of the tissue from which they are obtained. Referred to as the Neurosphere Assay (NA) it has provided a wealth of data on the existence of neural stem cells and on their potential for therapeutic use.

Briefly, the NA involves the microdissection of embryonic through to adult CNS tissue followed by the disruption of cell to cell contacts and the generation of a suspension of single cells. Cells are plated (typically at a low density) in tissue cultureware in a defined serum-free medium in the presence of at least one proliferation-inducing growth factor (ie. Epidermal Growth Factor [EFG], basic Fibroblastic Growth Factor [bFGF] etc.). Under these conditions within 2-5 days a multipotent NSC begins to divide giving rise to a clonally derived cluster of undifferentiated cells referred to as a neurosphere (FIG. 1). In the continued presence of the proliferation inducing factor the cells in the neurosphere continues to divide resulting in an increase in the number of cells comprising the neurosphere and consequently the size of the neurosphere. Neurospheres can be collected, disrupted in to a single cell suspension, and the cells replated in culture to generate new neurospheres. Passaging of NSC in this manner results in an arithmetic increase in viable CNS precursor cells (FIG. 3).

The NA has become the standard assay for the isolation of mammalian NSC and forms the core of many assays used to understand the cellular and molecular biology of stem cells in the nervous system. For instance, it has been used to screen exogenous signaling factors for their effects on stem cell function (Shimazaki, et. al., 2001) and to help understand the in vivo biology of neural stem cells (Morshead, et. al., 1994; Alvarez-Buylla et. al., 2001). While this assay has proven valuable in advancing the field it suffers from a significant limitation.

As a population, neurospheres can be passaged at least 10 times resulting in the generation of a large number of progeny that can be subsequently differentiated into the three primary cell types found in the mammalian CNS—neurons, astrocytes and oligodendrocytes—thereby satisfying the primary requirements of a stem cell (Reynolds and Weiss, 1996). In addition, individual clonally derived spheres can be dissociated into single cells and in the presence of a mitogenic factor, new spheres are generated (self-maintenance) and the progeny can be differentiated into neurons, astrocytes and oligodendrocytes. It is currently assumed that every sphere generated in the NA is derived from a NSC. The inventors have unexpected results indicating that this is not true and that the proliferative potential of the neurospheres generated in a NA vary. Hence, while the NA identifies NSC not all neurospheres generated in this assay are derived from a NSC. Some (and maybe the majority) of the neurospheres may be neural progenitor cells with a more limited proliferative potential and possibly a different differentiation potential as well. The number of NSC determined by a NA is an overestimation and subsequent interpretations based on the results are likely to be incorrect. For instance, FIGS. 2A and 2B are representative of a population of neurospheres generated in the NA. As a hypothetical example lets say the difference between FIGS. 2A and 2B is the addition of a polypeptide growth factor called GF-X in 2B. In this case it would appear that the addition of GF-X resulted in an approximate 34% reduction in the number of neurospheres. This would be interpreted as a negative regulatory effect of GF-X on the proliferation or survival of NSC in this particular experiment. This interpretation would be correct if all neurospheres generated in the NA were derived from stem cells, however, if they are not the conclusion is invalid. An example of such an experiment can be found in U.S. Pat. No. 5,851,832 Example 43. In both of these cases change in the number of neurospheres is assumed to reflect an effect on NSC, however, unless all neurospheres generated in the NA are shown to be derived from stem cells this assumption is unfounded. Hence, a significant deficiency exists in the currently used method to study NSC.

Therefore, in view of the aforementioned deficiency attendant with prior art methods of studying NSC in vitro, a need exists in the art for an in vitro assay that can differentiate between NSC and neural progenitor cells.

A need also exists for an assay that can differentiate between different NSC based on their proliferative potential.

SUMMARY OF THE INVENTION

The present invention provides an assay that can be used to identify, discriminate, isolate, and quantify types of neural stem and progenitor cells.

This invention relates to a method for the in vitro culture and proliferation of neural stem cells and neural progenitor cells in a three dimensional semi-solid medium (e.g. see the method shown in FIG. 12). In one aspect, this invention relates to a method to identify neural stem cells and to be able to differentiate them from progenitor cells. In another aspect, this invention relates to a method of identifying neural stem cells with varying degrees of proliferative potential and to be able to discriminate between neural stem cells with a high proliferative potential and those with a lower or lesser proliferative potential. In another aspect this invention relates to a method to discriminate between types of NSC and types of neural progenitor cells based on colony size, morphology and antigen expression.

Accordingly, the present invention provides a method for identifying neural stem cells or neural progenitor cells comprising:
(a) suspending neural cells in a semi-solid medium which supports the growth of neural cells;
(b) plating the cells in the semi-solid medium at a density that allows for the production of colonies;
(c) culturing the plated cells until size differences can be discerned between the colonies; and
(d) estimating colony size wherein the larger colonies are likely produced by neural stem cells and wherein the smaller colonies are likely produced by neural progenitor cells.

As an alternate embodiment, the criteria for the identification and discrimination of types of NSC from types of neural progenitor cells can be based on the morphologies of colonies produced by the cells within the initial colonies.

Accordingly, the present invention also provides a method for identifying neural stem cells or neural progenitor cells comprising:
(a) suspending neural cells in a semi-solid medium which supports the growth of neural cells;
(b) plating the cells in the semi-solid medium at a density that allows for the production of colonies;
(c) culturing the plated cells until colonies are formed; and
(d) determining the morphology of the colonies wherein the presence of undulated colonies indicates that the colonies are likely produced by neural stem cells and wherein the presence of colonies with a smooth periphery indicates that the colonies are likely produced by neural progenitor cells.

In another embodiment of the invention, the presence of neural stem cells or neural progenitor cells can be determined by detecting the presence of a marker associated with undifferentiated or differentiated cells on the colonies. Accordingly, the present invention also provides a method for identifying neural stem cells or neural progenitor cells comprising:
(a) suspending neural cells in a semi-solid medium which supports the growth of neural cells;
(b) plating the cells in the semi-solid medium at a density that allows for the production of colonies;
(c) culturing the plated cells until colonies are formed; and
(d) determining the antigen expression of the colonies wherein the presence of markers associated with undifferentiated cells indicates that the colonies are likely produced by neural stem cells and wherein the presence of markers associated with differentiated cells indicates that the colonies are likely produced by neural progenitor cells.

Examples of antigen expression which relate to undifferentiated cells and neural lineages include nestin, sox2, Musashi, ABCG2, LeX, PNA, CD24 and other markers. Examples of antigen expression which relate to differentiated cells of the CNS include Beta-Tubulin, GFAP, O4, MAP2 and MBP and others.

This invention provides an in vitro method for the isolation, proliferation and expansion of neural stem cells or neural progenitor cells and their progeny in a semi-solid 3-D matrix. The invention also provides a method to allow for the discrimination of NSC with High Proliferative Potential (HPP) from NSC with low proliferative potential and to distinguish between stem cells and types of neural progenitor cells.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE FIGURES

The invention will now be described in relation to the drawings in which:

FIG. 2A is a microphotograph of a culture which generated 35 neurospheres in a 200 microliter well while in another culture only 23 neurospheres were generated (FIG. 2B).

(A) At 2 days in vitro (DIV) a number of small spheres, which are attached to the substrate, are beginning to form in the Neurosphere Assay. Inset upper left hand corner is a higher magnification of a 2 DIV neurosphere.

(B) By 4 DIV the clonal clusters have grown in size, most have detached from the substrate and are floating in suspension. A higher magnification of a 4 DIV neurosphere is shown in the inset upper left hand corner.

(C) By 5-7 DIV most of the neurospheres are floating in suspension. At this stage they are ready to be passaged.

(D) A dividing cell at 1 DIV in the NCFC Assay.

(E) By 7 DIV colonies in the NCFC Assay are well defined and can range from 40 µm to 500 µm in diameter (F) By 14 DIV many of the colonies in the NCFC Assay remain relatively small, while others continue to grow in size.

Figure 5:
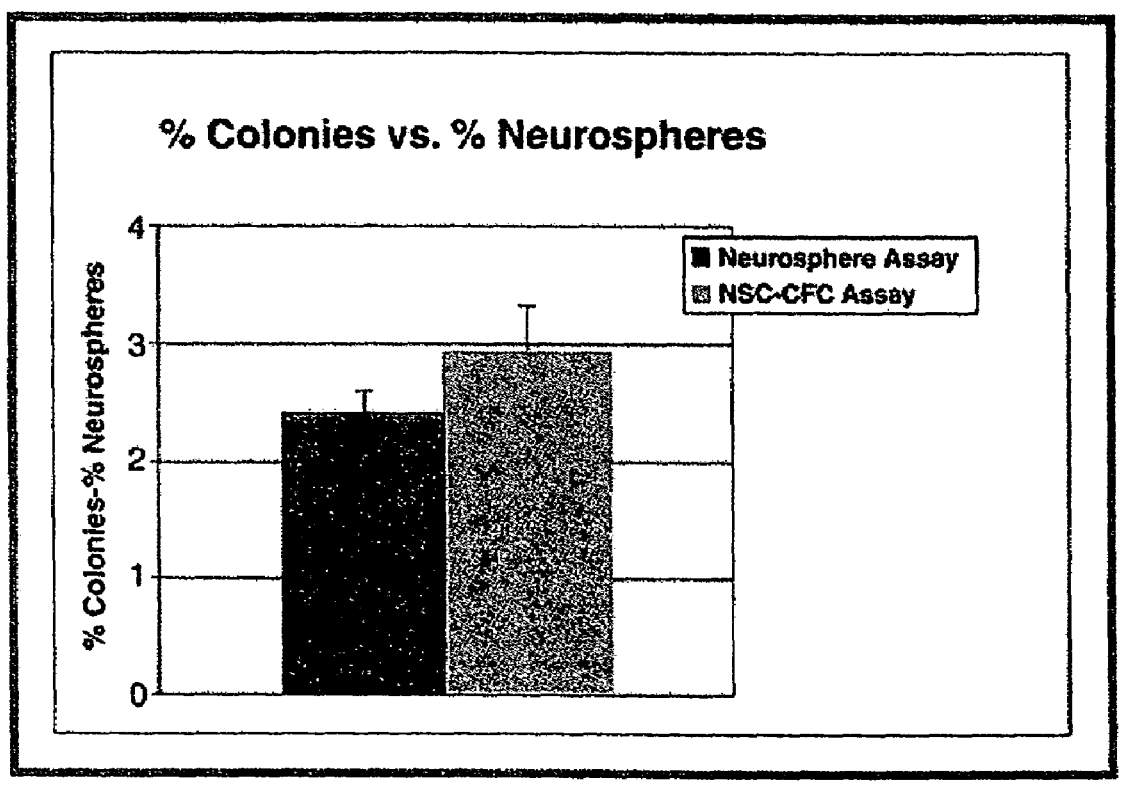

FIG. 5: The number of colonies/spheres generated by mouse embryonic day 14 striatal cells in the NCFC Assay and the Neurosphere Assay are similar. In the Neurosphere Assay 2.4±0.9% (mean±SE; number of spheres/total cells plated) of the cells formed neurospheres, while 2.8±1.2% (mean±SE) of plated cells formed colonies in the NCFC Assay.

Figure 6:
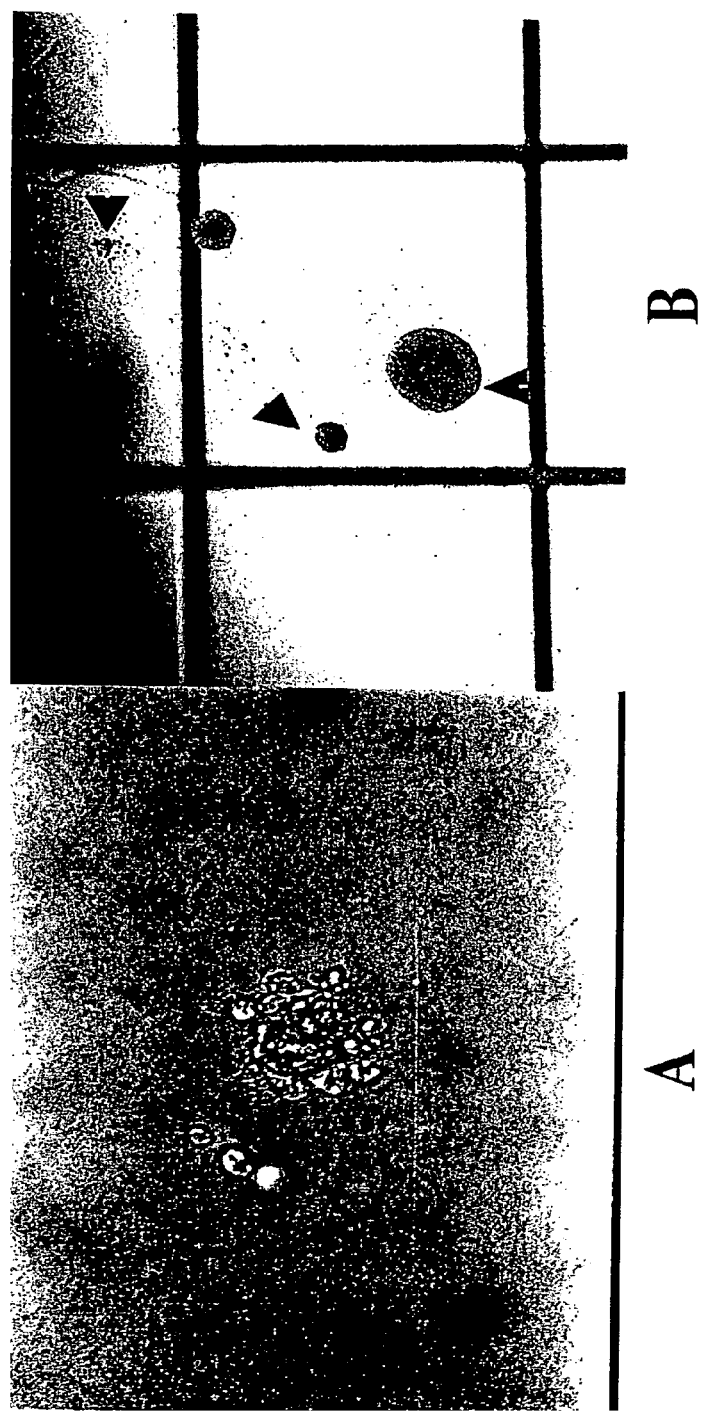

FIG. 6: Seven and 14 day old colonies generated by mouse day 14 embryonic striatal cells grown in NCFC Assay. Microphotographs of colonies seven (A) and 14 (B) days after plating. At 14 days 3 different colony sizes can be identified (arrows).

Figure 7:
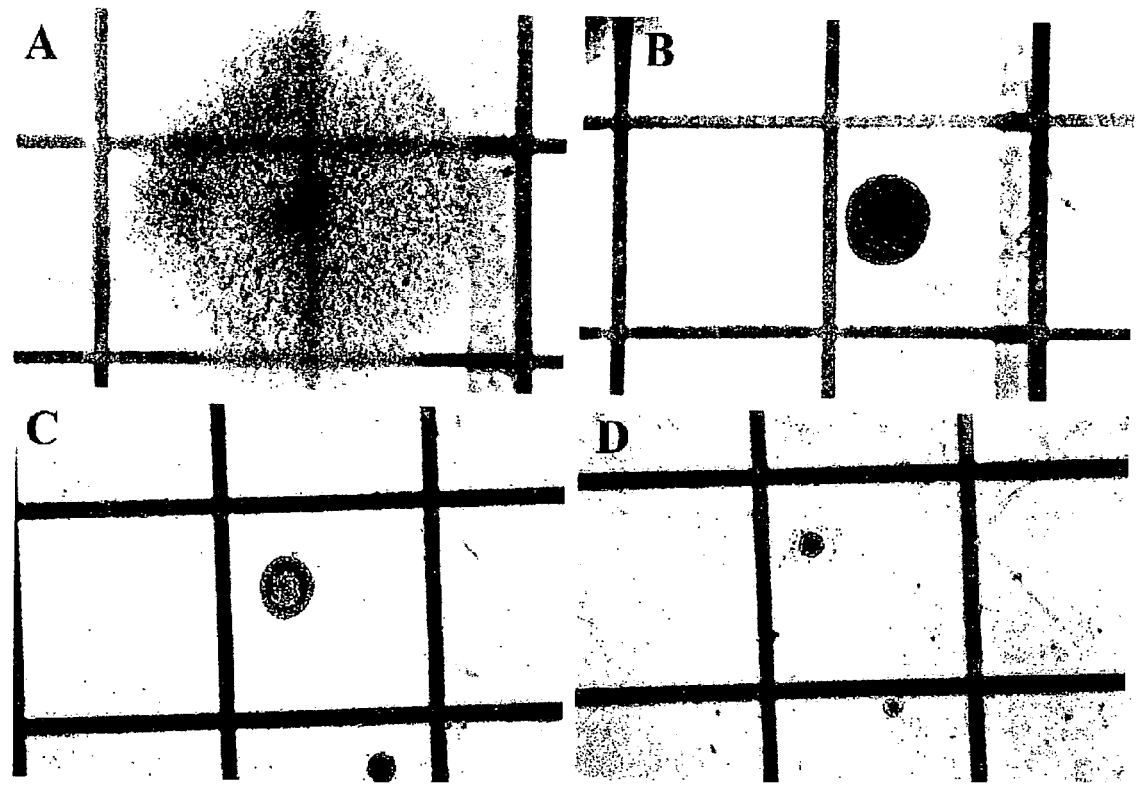

FIG. 7: Comparison of colony sizes generated by mouse day 14 embryonic striatal cells in the NCFC Assay. Based on diameter of individual colonies a wide range of colony size was observed in this assay. For descriptive purposes the inventors created four groupings:

(A) greater than 2 mm
(B) 1-2 mm
(C) 0.5-1 mm and
(D) less than 0.5 mm.

Figure 8:
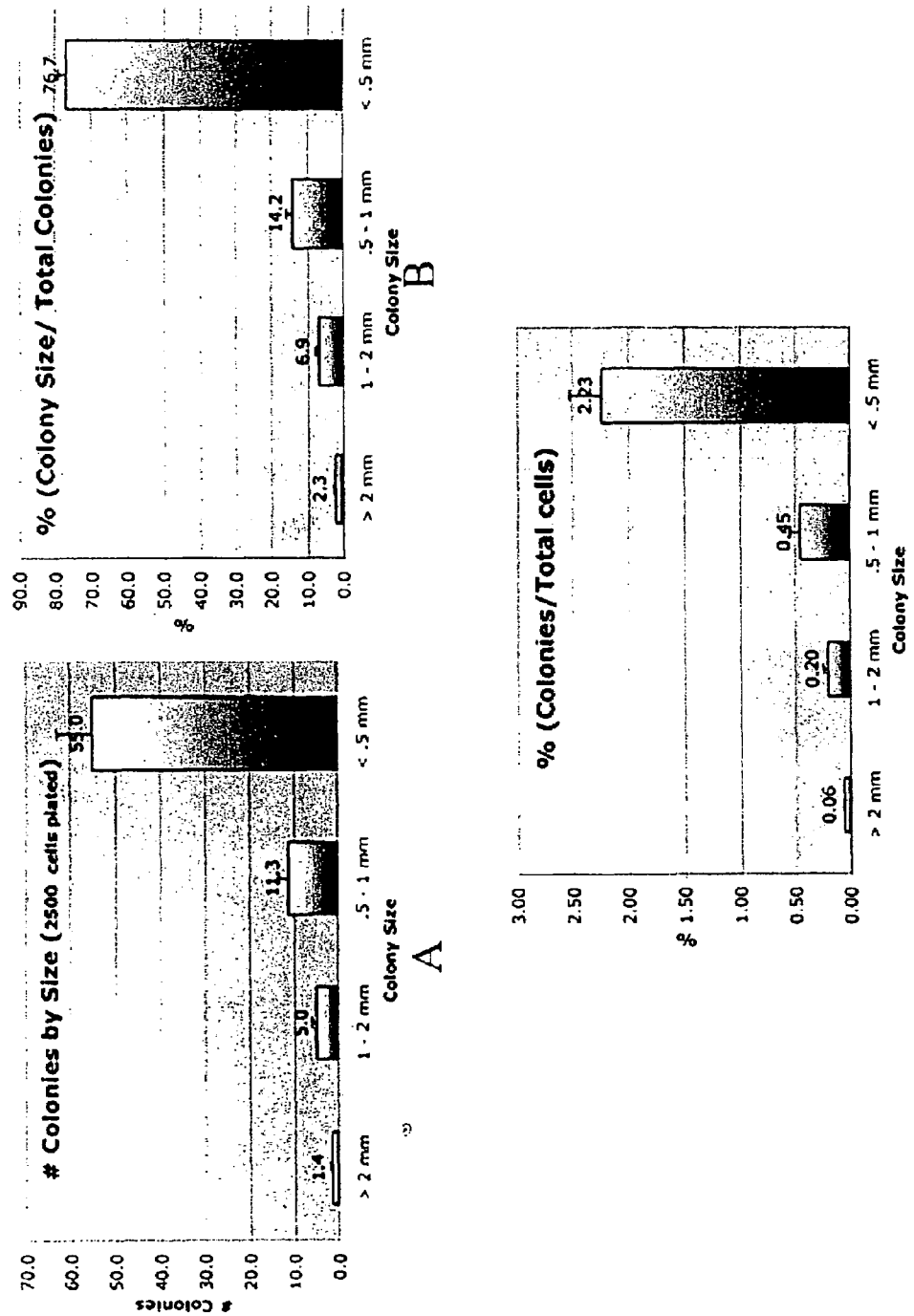

FIG. 8: The relative frequency of colonies within each of the four size categories generated by mouse day 14 embryonic striatal cells in the NCFC Assay:

(A) 2500 cells were plated in NCFC Assay medium as described below. Twenty-one days later the number of colonies in four different size groupings were counted.

(B) When the data in FIG. 6A is expressed as a percentage of the size of colonies over total number of colonies greater than 70% of the colonies were less than 0.5 mm in diameter while large, highly proliferative colonies accounted for approximately 2% of the total.

(C) The frequency (%) of colonies (subdivided by colony size as in FIG. 7) relative to total number of cells plated reveals that less than 3% of the total cells plated proliferated and formed colonies. Of this 3%, the majority (2.23%) produced small colonies (<0.5 mm in diameter) suggesting a more limited proliferative potential. These colonies remained small. A very small fraction (0.06%) of the total cells plated were highly proliferative and formed large (>2 mm) colonies.

Figure 9:
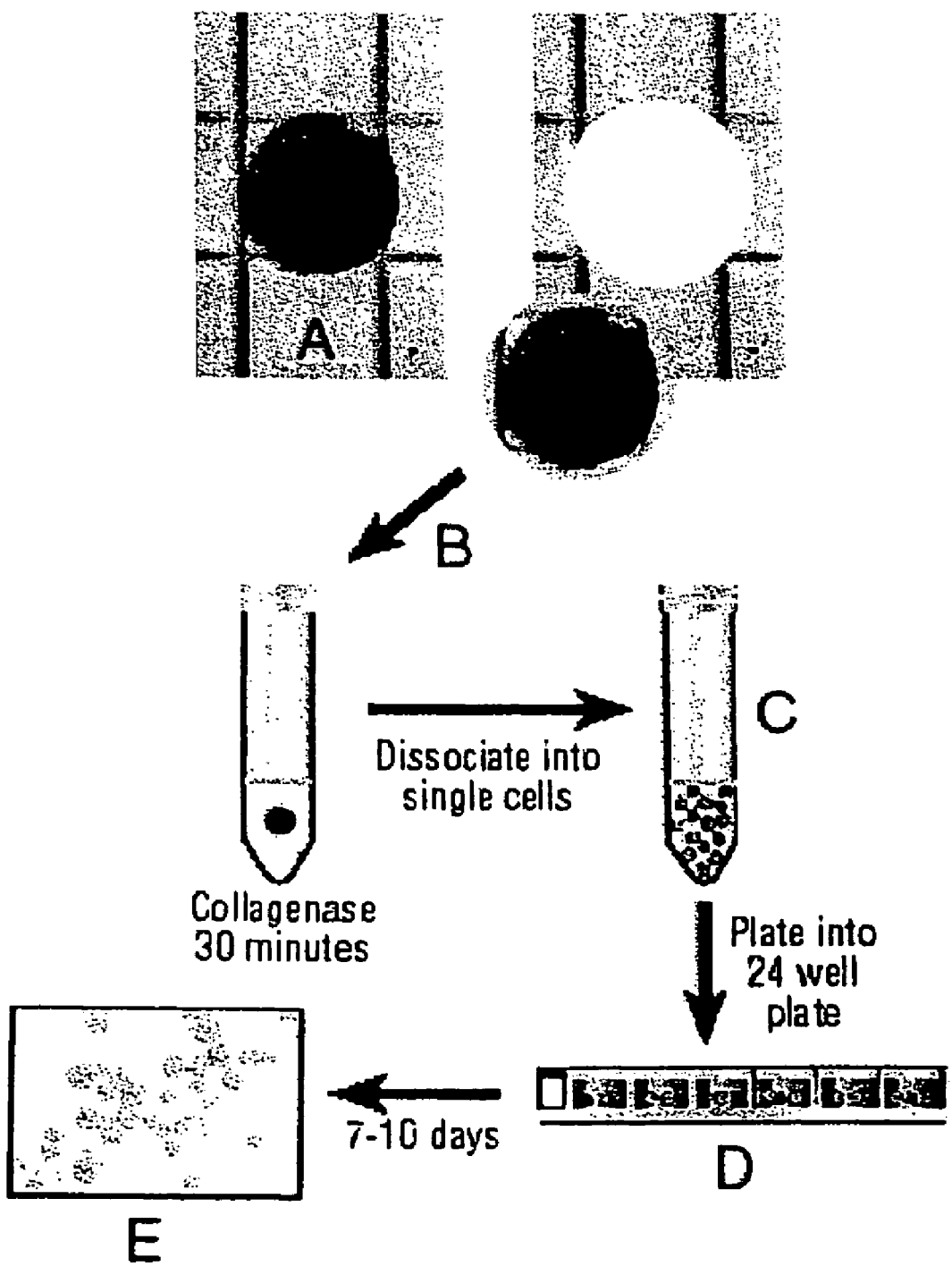

FIG. 9: Identification and excising of colonies generated by mouse day 14 embryonic striatal cells in the NCFC Assay and subsequent passage of the cells dissociated from the colony in liquid medium.

(A) Colonies of interest were identified under a dissecting microscope and under sterile conditions the colony were cut from the semi solid matrix with a pair of microdissecting scissors.

(B) The excised colony was transferred to a collagenase solution and incubated at 37° C. for 30 mins.

(C) The colony was disrupted with a 200 ul Gilson pipette tip breaking up the matrix and creating a single cell suspension.

(D) Cells were plated in a single well of a 24 well plate in a defined serum free medium containing EGF.

(E) Seven to 10 days later neurospheres were generated.

Figure 10:
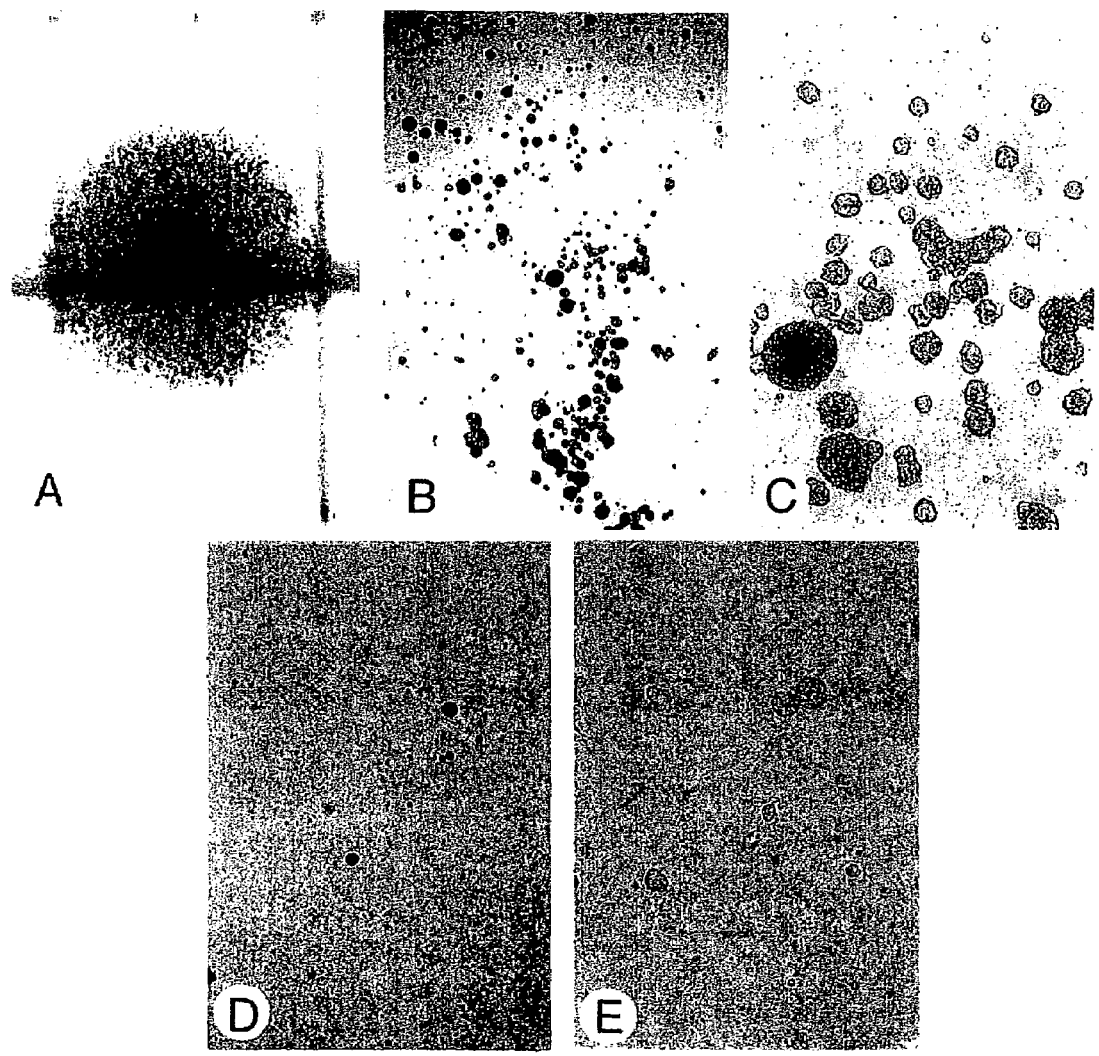

FIG. 10: The generation of secondary and tertiary spheres from a High Proliferative Potential (HPP) colony generated by mouse day 14 embryonic striatal cells:

(A) A HPP colony (2.1 mm diameter) prior to being excised.

(B) Dissociated cells from (A) have formed a large number of neurospheres (secondary colonies) at 7 DIV.

(C) A higher magnification of a region in (B).

(D) Neurospheres from (B) were passaged in liquid culture generating tertiary neurospheres at 7 DIV.

(E) Higher magnification of a region in (D).

Figure 11:
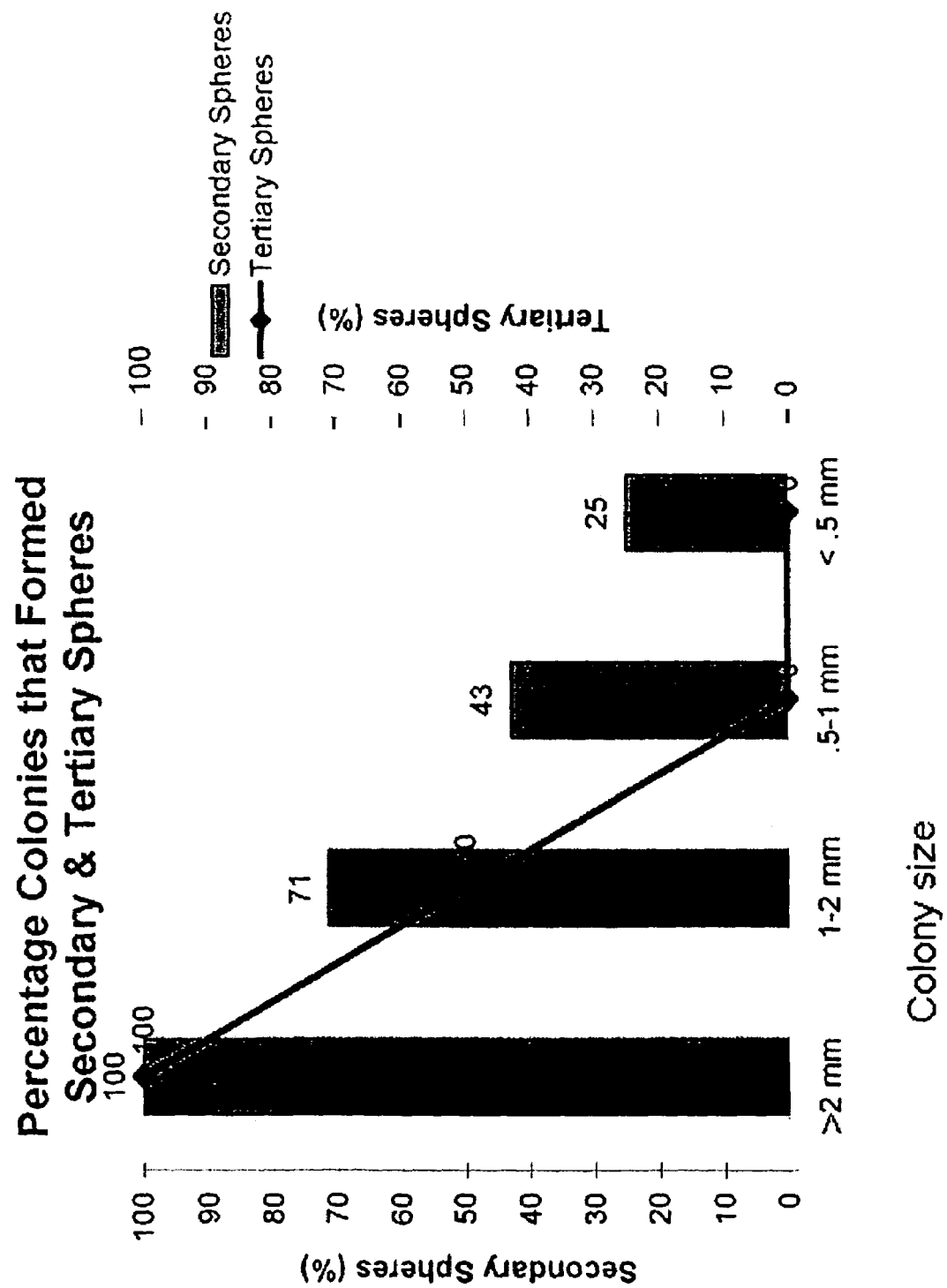

FIG. 11: Percentage of colonies generated by cultured mouse day 14 embryonic striatal cells that generated seconday and tertiary neurospheres. 100% of colonies greater than 2 mm in diameter generated secondary colonies, with colonies between 1-2, 0.5-1 and those less than 0.5 mm produced secondary spheres 71, 43 and 25 percent of the time, respectively. Tertiary colony formation was seen only in those greater than 2 mm and 1-2 mm in diameter (100% and 50% of the time, respectively). No tertiary sphere formation was seen in colonies less than 1 mm in diameter.

Figure 12:
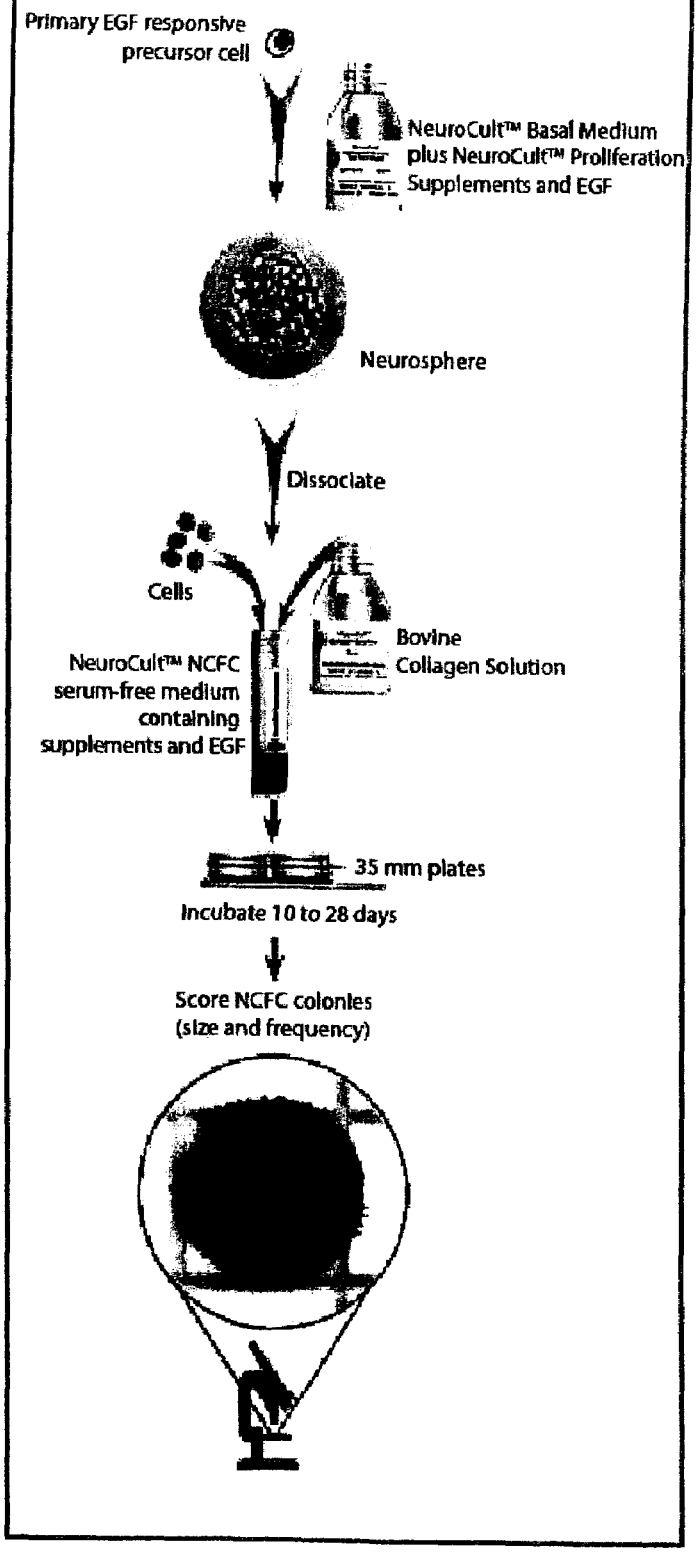

FIG. 12 is a schematic diagram of an embodiment of the method of the invention.

Figure 13:
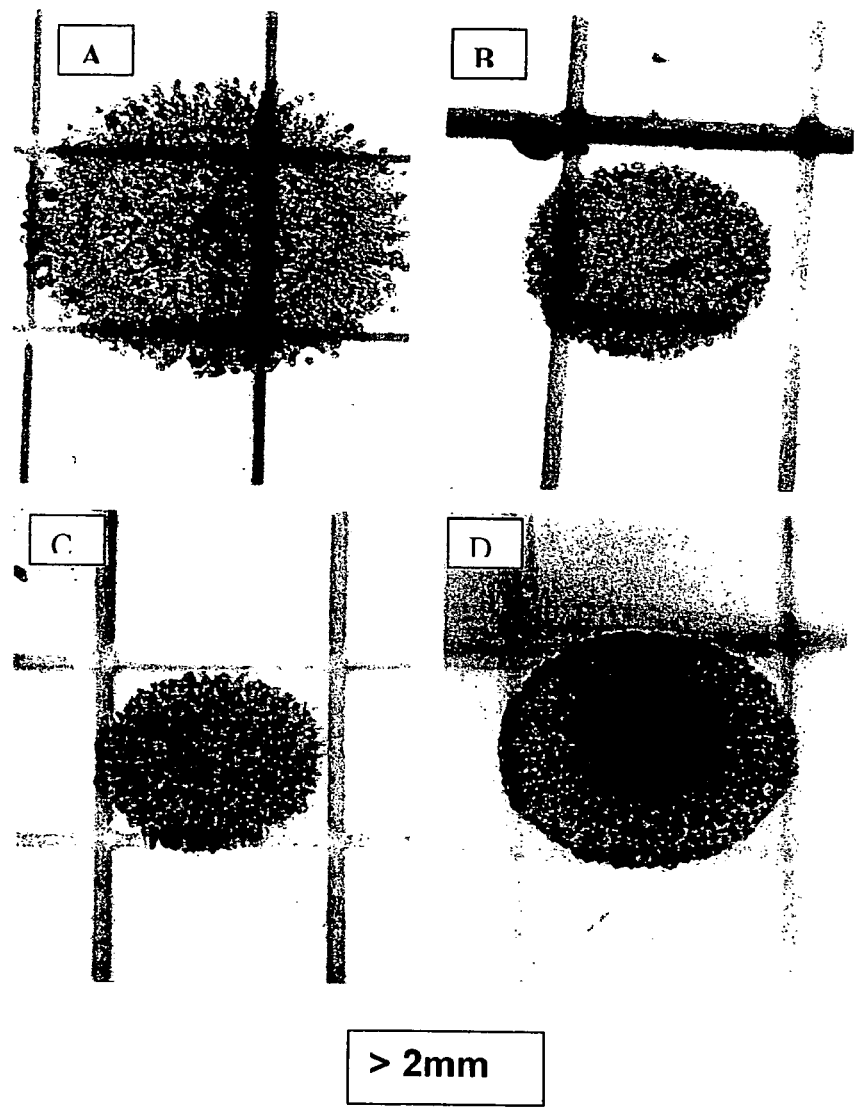

FIG. 13: Different colony morphologies observed for colonies >2 mm in diameter generated by mouse day 14 embryonic striatal cells. A variety of colony morphologies is observed among colonies categorized as >2 mm in diameter.

Figure 14:
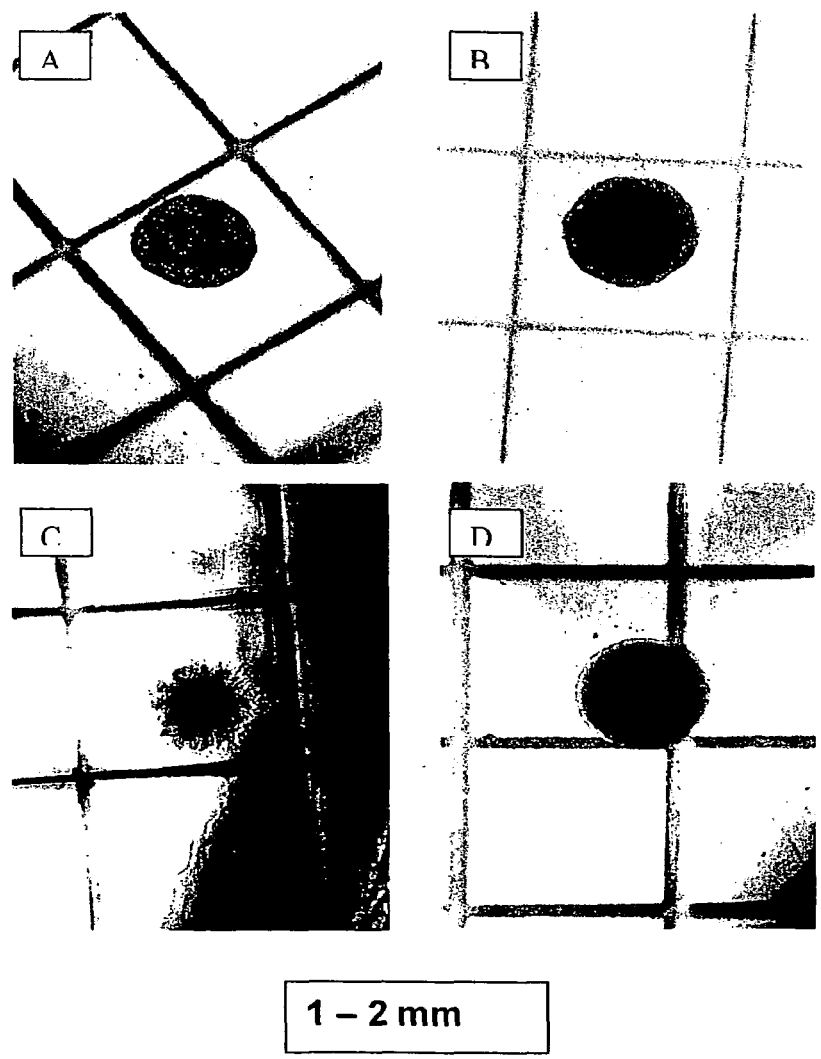

FIG. 14: Different colony morphologies observed for colonies 1-2 mm in diameter generated by mouse day 14 embryonic striatal cells. A variety of colony morphologies is observed among colonies categorized as 1-2 mm in diameter.

Figure 15:
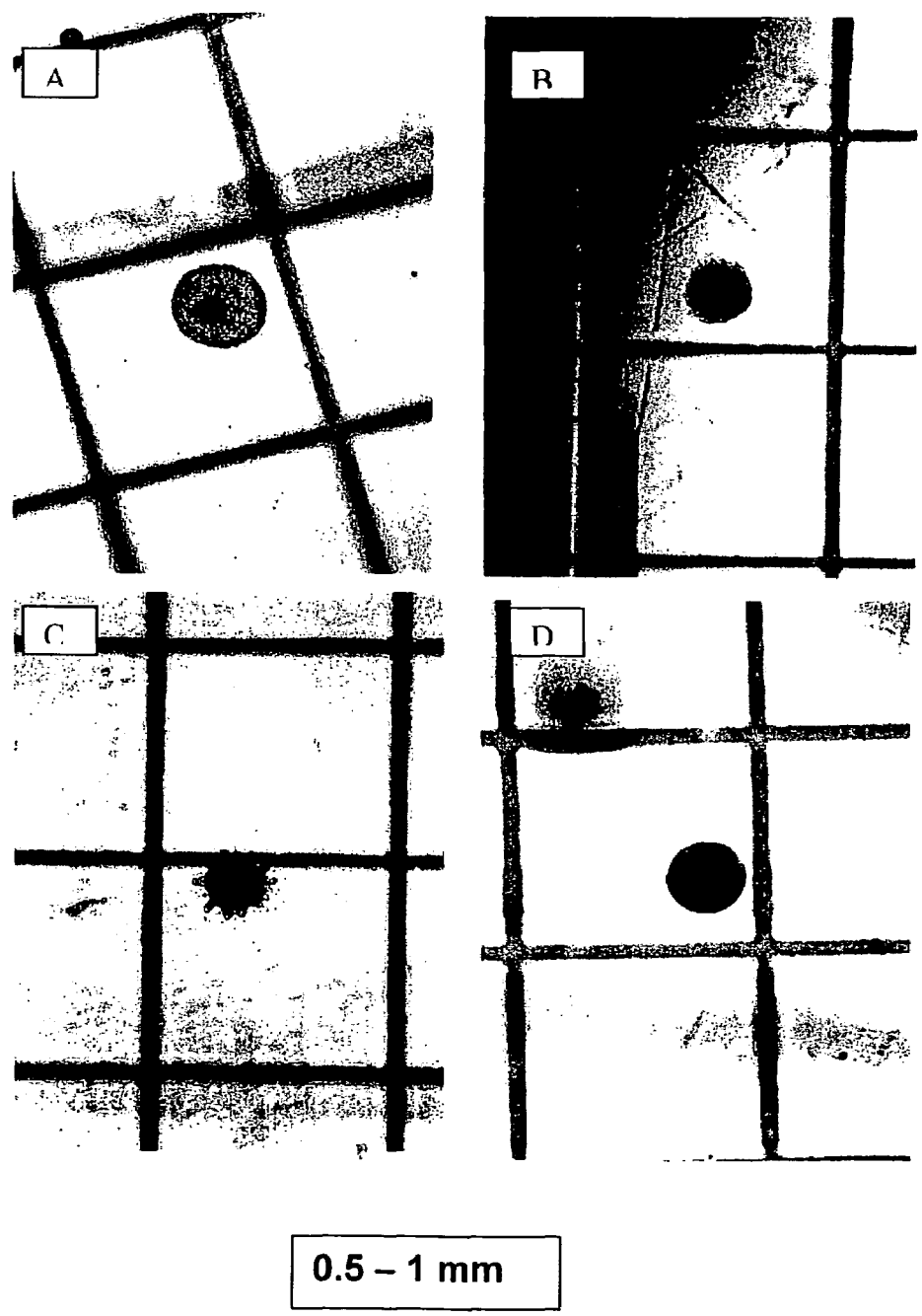

FIG. 15: Different colony morphologies observed for colonies 0.5-1 mm in diameter generated by mouse day 14 embryonic striatal cells. A variety of colony morphologies is observed among colonies categorized as 0.5-1 mm in diameter.

Figure 16:
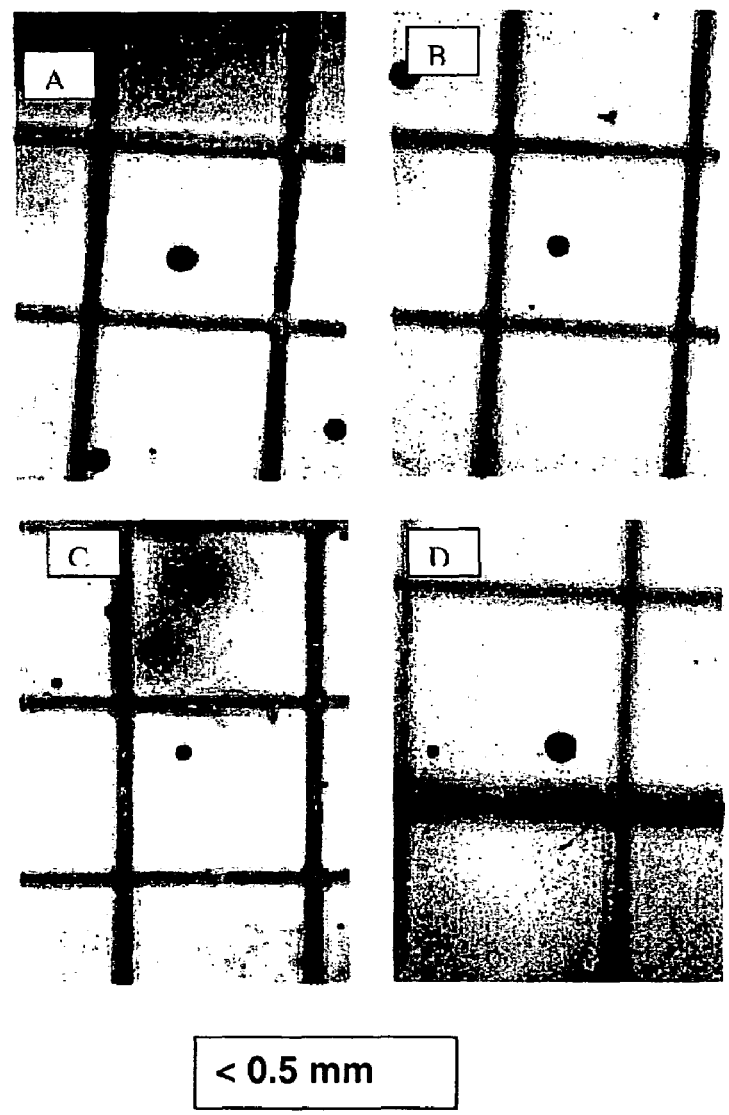

FIG. 16: Different colony morphologies observed for colonies <0.5 mm in diameter generated by mouse day 14 embryonic striatal cells. A variety of colony morphologies is observed among colonies categorized as <0.5 mm in diameter.

Figure 17:
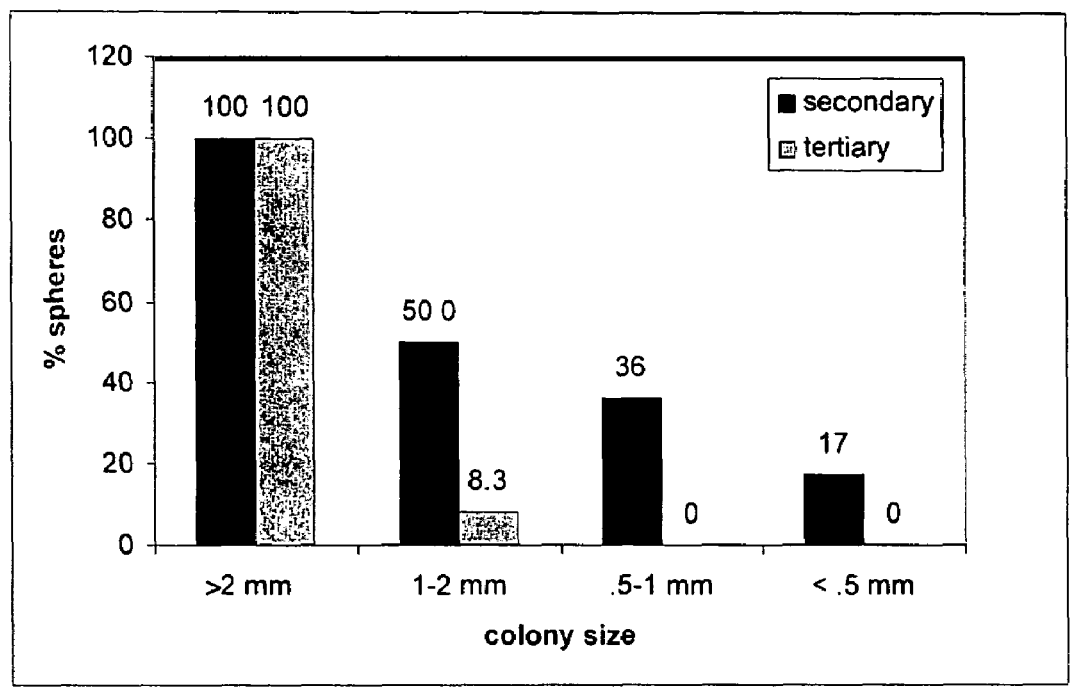

FIG. 17: Percentage of colonies generated by primary mouse day 14 embryonic striatal cells that generated secondary and tertiary neurospheres. 100% of colonies greater than 2 mm in diameter generated secondary colonies, with colonies between 1-2, 0.5-1 and those less than 0.5 mm produced secondary spheres 50, 36 and 17 percent of the time, respectively. Tertiary colony formation was seen only in those greater than 2 mm and 1-2 mm in diameter (100% and 8.3% of the time, respectively). No tertiary sphere formation was seen in colonies less than 1 mm in diameter.

Figure 18:
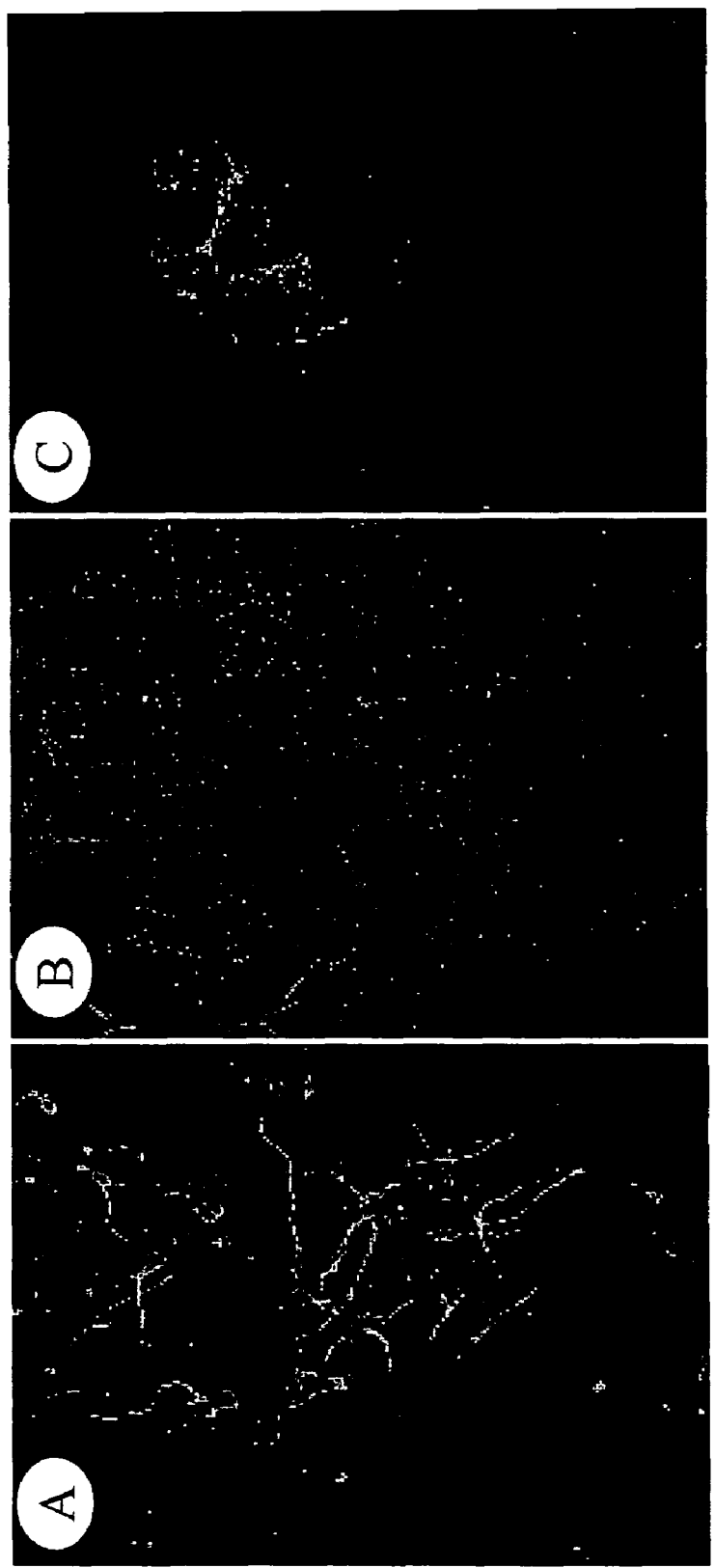

FIG. 18: Immunostaining of mouse day 14 embryonic striatal cells from secondary spheres generated from colonies >2 mm in diameter. Figure legend: Staining of neurons stained with Beta-Tubulin antibody are shown in red (A), staining of astrocytes stained with glial fibrillary acidic protein (GFAP) antibody are shown in green (B) and staining of oligodendrocytes stained with O4 antibody are shown in blue (C).

Figure 19:
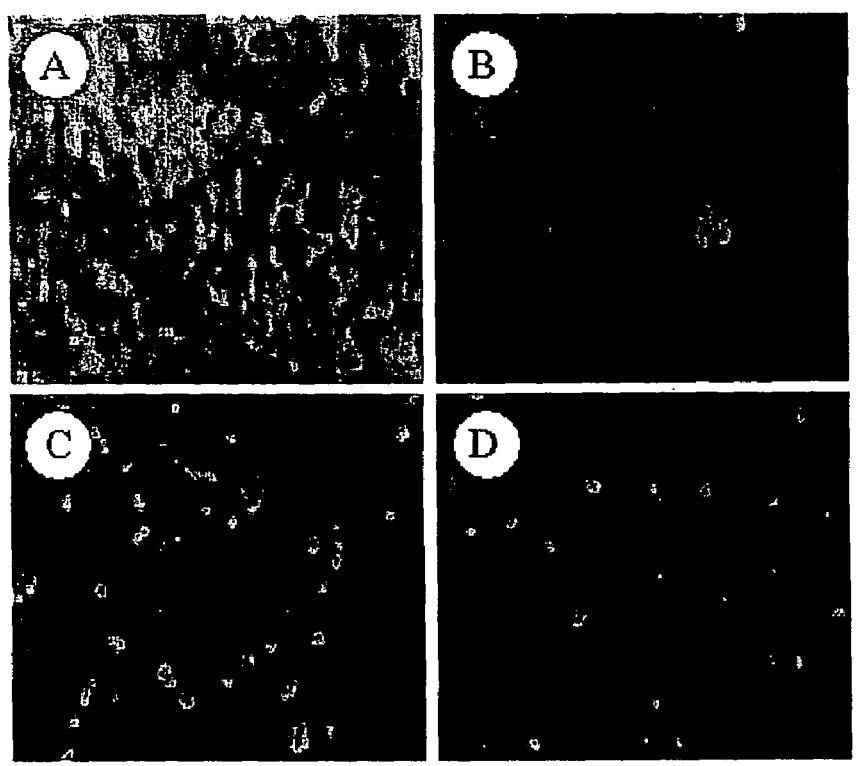

FIG. 19: In situ immunostaining of colonies generated by mouse day 14 embryonic striatal cells in the NCFC assay.

Staining of undifferentiated cells within a colony>2 mm in diameter (A), 1-2 mm in diameter (B), 0.5-1 mm in diameter (C) and<0.5 mm in diameter (D) generated by mouse day 14 embryonic striatal cells and stained with nestin antibody are shown in red.

Figure 20A:
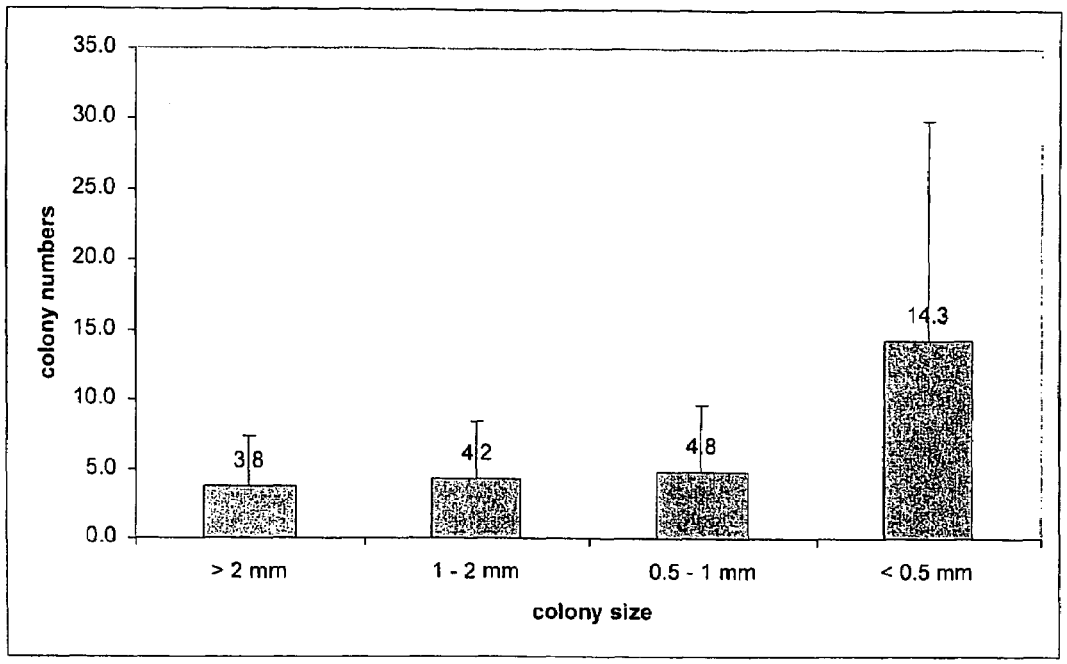

FIG. 20: The relative frequency of colonies generated by mouse day 14 embryonic striatal cells within each of the four size categories in NCFC Assay:
  (A) 7500 cells were plated in NCFC Assay medium as described in Example 12 below. Twenty-one days later the colonies were assigned to four size categories and number of colonies in four different size groupings were counted (mean±SD).
  (B) When the number of colonies in a given size category (FIG. 20A) is expressed as a percentage of the total number of colonies 50% of the colonies were less than 0.5 mm in diameter while colonies >2 mm in diameter accounted for approximately 16% of the total colonies (mean±SD).
  (C) The frequency (%) of colonies (in the given size categories) per total number of cells reveals that less than 0.6% of the total cells plated proliferated and formed colonies. Of this 0.6%, the majority (0.29%) produced small colonies (<0.5 mm in diameter) suggesting a more limited proliferative potential. These colonies remained small. A very small fraction (0.08%) of the total cells plated were highly proliferative and formed large (>2 mm) colonies (mean±SD).

Figure 21:
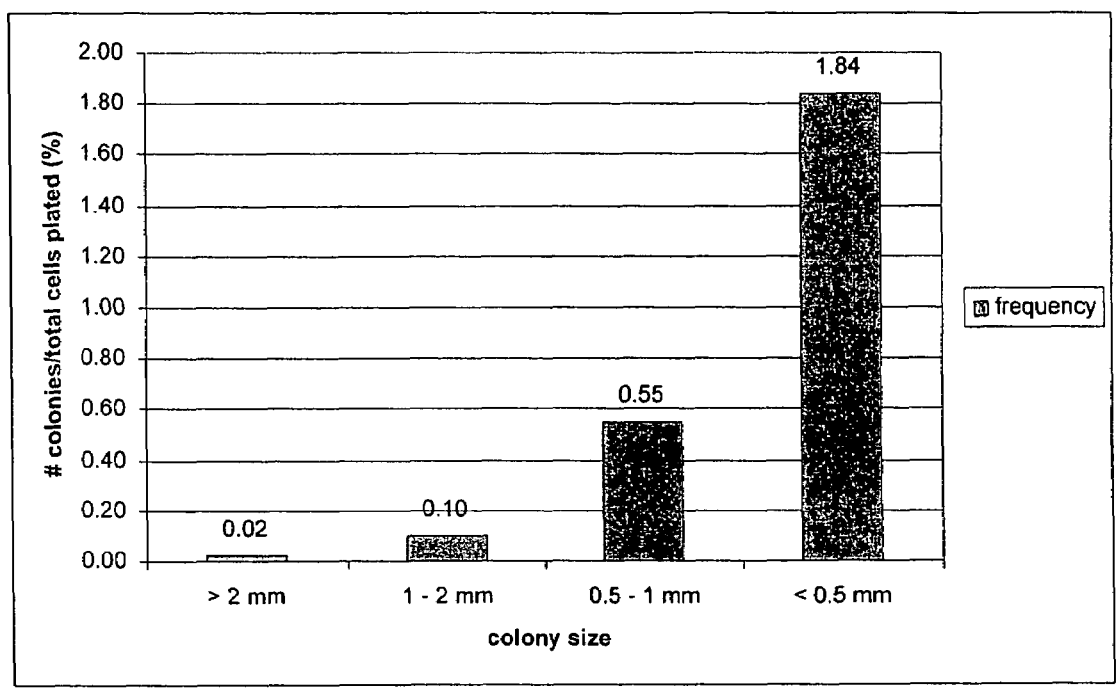

FIG. 21: Mouse day 14 embryonic striatal cells which produced colonies >2 mm were isolated from the NCFC assay, dissociated and cultured for 3 passages in liquid suspension cultures (Neurosphere Assay) to generate tertiary neurospheres. The tertiary neurospheres were dissociated into a single cell suspension, counted and 2500 cells were plated in the NCFC assay for 21 days. FIG. 21 shows the frequency of colonies (in the given size categories) formed by 2500 cells obtained from tertiary neurospheres generated from the cells in colonies >2 mm in diameter in the initial NCFC assay. Cells from colonies >2 mm in diameter were capable of generating colonies of the four categories when re-plated in the NCFC assay. The frequency (%) of colonies (in the designated size categories) relative to total number of cells reveals that 2.5% of the total cells plated (mean±SD) proliferated and formed colonies. Of this 2.5%, the majority (1.8%) produced small colonies (<0.5 mm in diameter) suggesting a more limited proliferative potential. These colonies remained small. A very small fraction (0.02%) of the total cells plated were highly proliferative and formed large (>2 mm) colonies.

Figure 22:
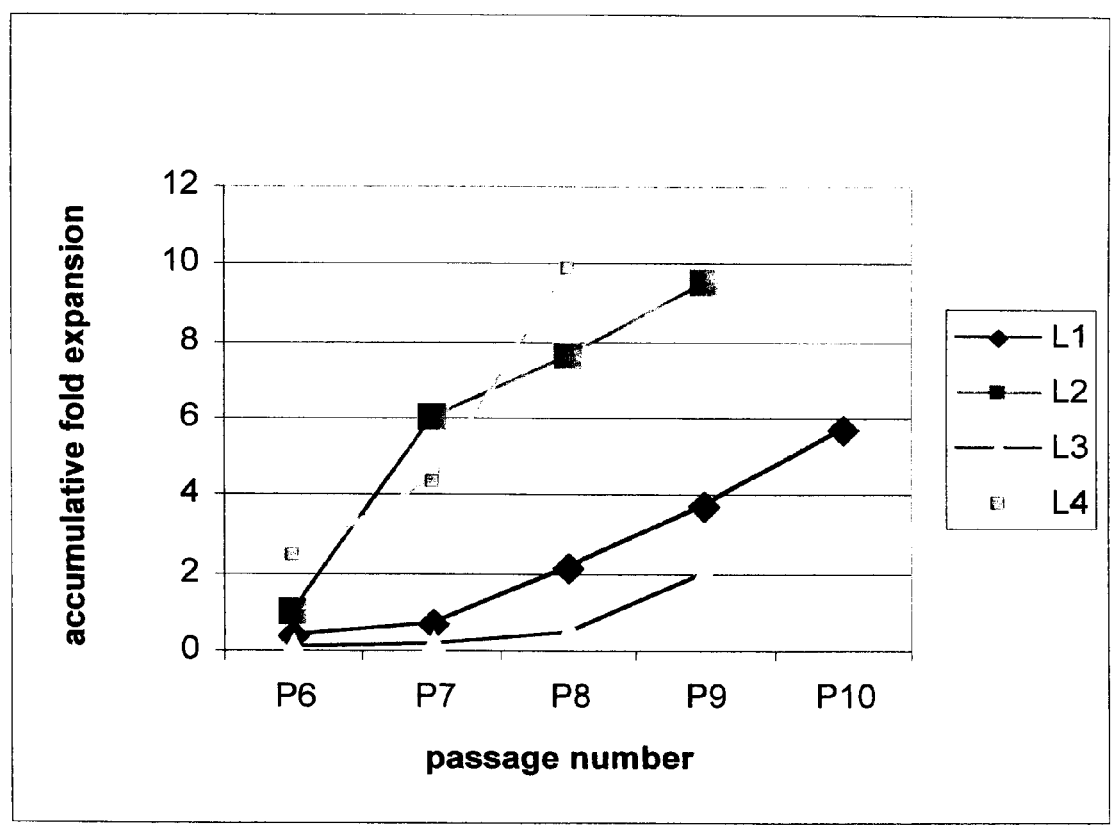

FIG. 22: Long term expansion in mouse embryonic day 14 striatal cells in liquid cultures (NA) initiated from cells within four colonies >2 mm in diameter (generated in the NCFC assay). Cells from four (described as Large (L)1, L2, L3 and L4) individual colonies >2 mm in diameter were passaged in long-term neurosphere (beyond passage 3) cultures showed high fold expansion by passage 6.

FIG. 23: NCFC colonies from embryonic day 18 (E18) rat cortical cells. Two colonies 1-2 mm in diameter (A, B) generated by E18 rat cortical cells in the NCFC assay.

Figure 24A:
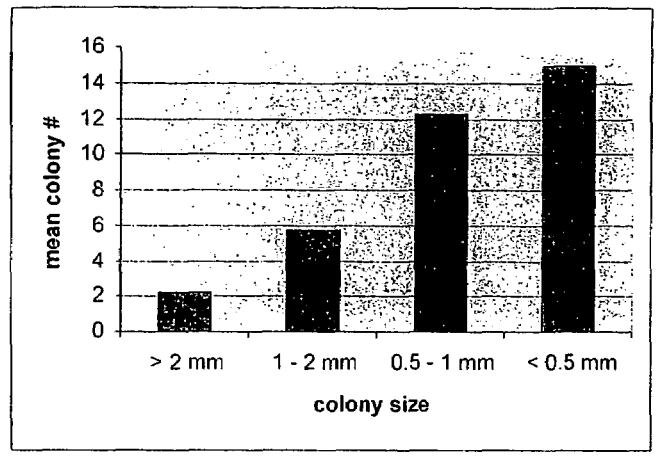

FIG. 24: The relative frequency of colonies within each of the four size categories from embryonic day 18 (E18) rat cortical cells in NCFC Assay:
  (A) 7500 cells were plated in NCFC Assay medium as described in Example 16. Twenty-one days later the number of colonies in four different size groupings were counted.
  (B) When the data in FIG. 24A is expressed as a percentage of colonies (in the given size categories) per total number of colonies, greater than 77% of the colonies were less than 0.5 mm in diameter while large, highly proliferative colonies accounted for approximately 0.2% of the total.
  (C) The frequency (%) of colonies (in the specified size categories) per total number of cells.

Figure 25:
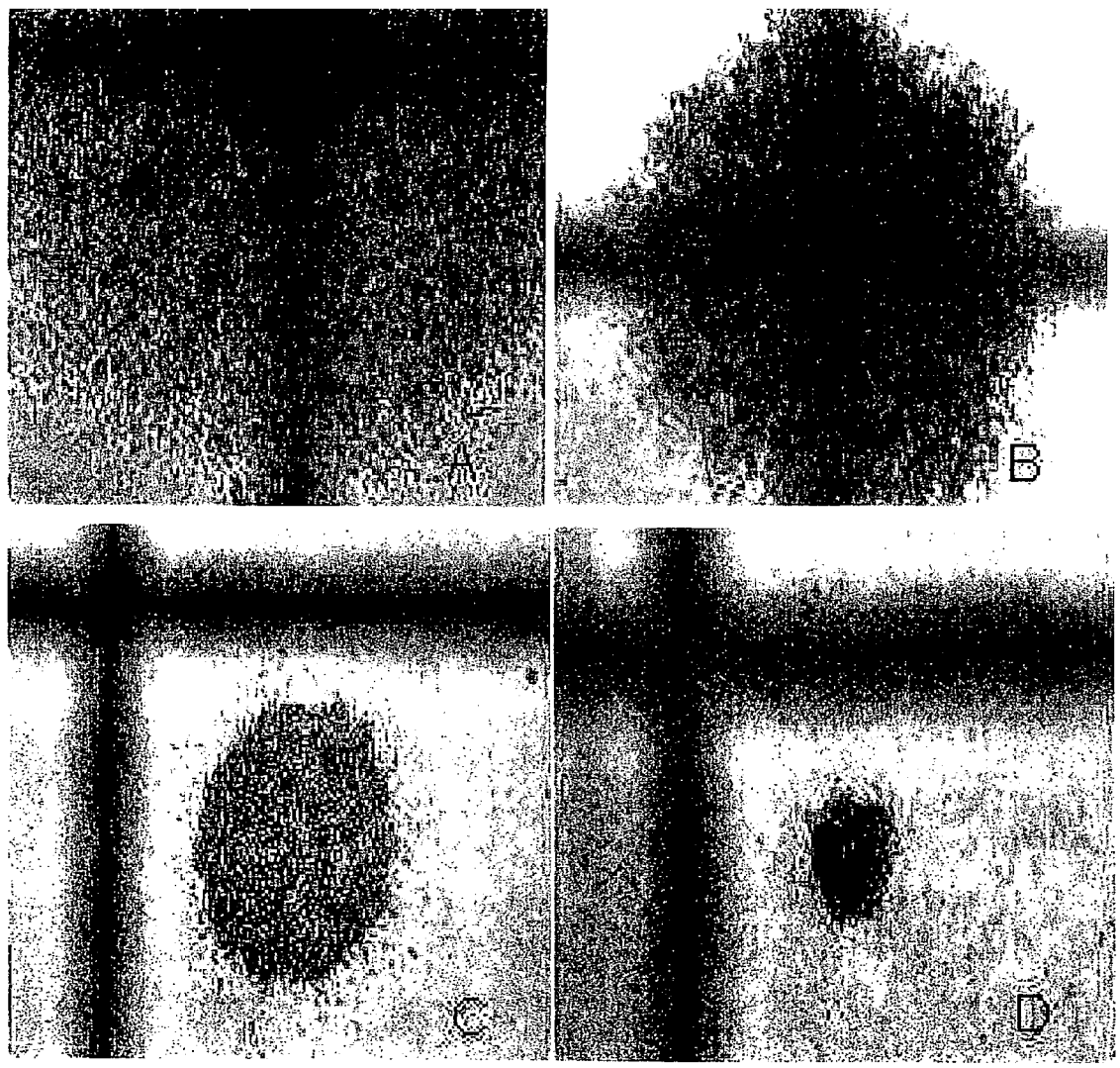

FIG. 25: The different sized colonies generated by adult subventricular zone (SVZ) mouse cells in the NCFC Assay:
  (A) greater than 2 mm
  (B) 1-2 mm
  (C) 0.5-1 mm and
  (D) less than 0.5 mm.

Figure 26:
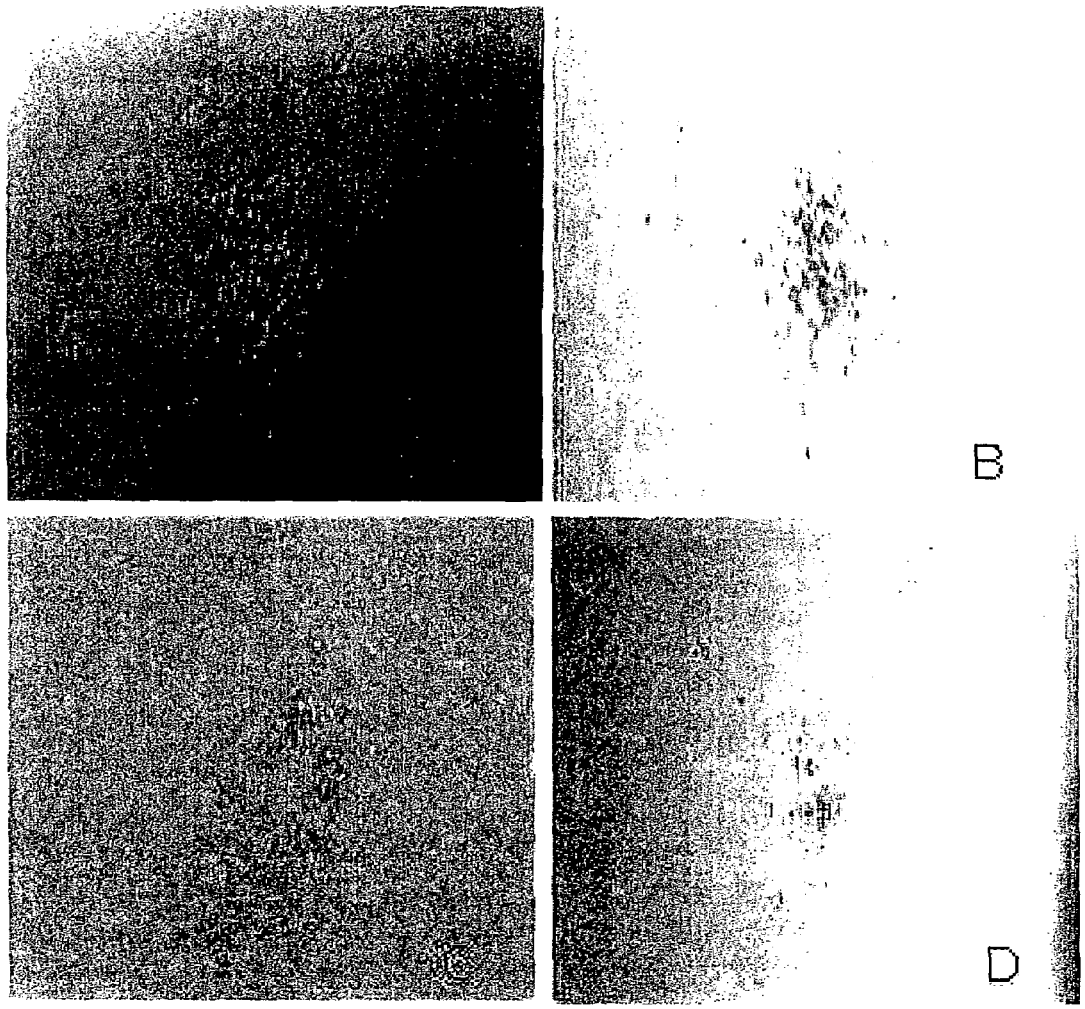

FIG. 26: The different sized colonies generated by fetal human cortical cells in the NCFC Assay. The cells within the different colonies generated are more dispersed compared to the colonies generated by adult and embryonic neural cells.
  (A) greater than 2 mm
  (B) 1-2 mm
  (C) 0.5-1 mm and
  (D) less than 0.5 mm.

Figure 27:
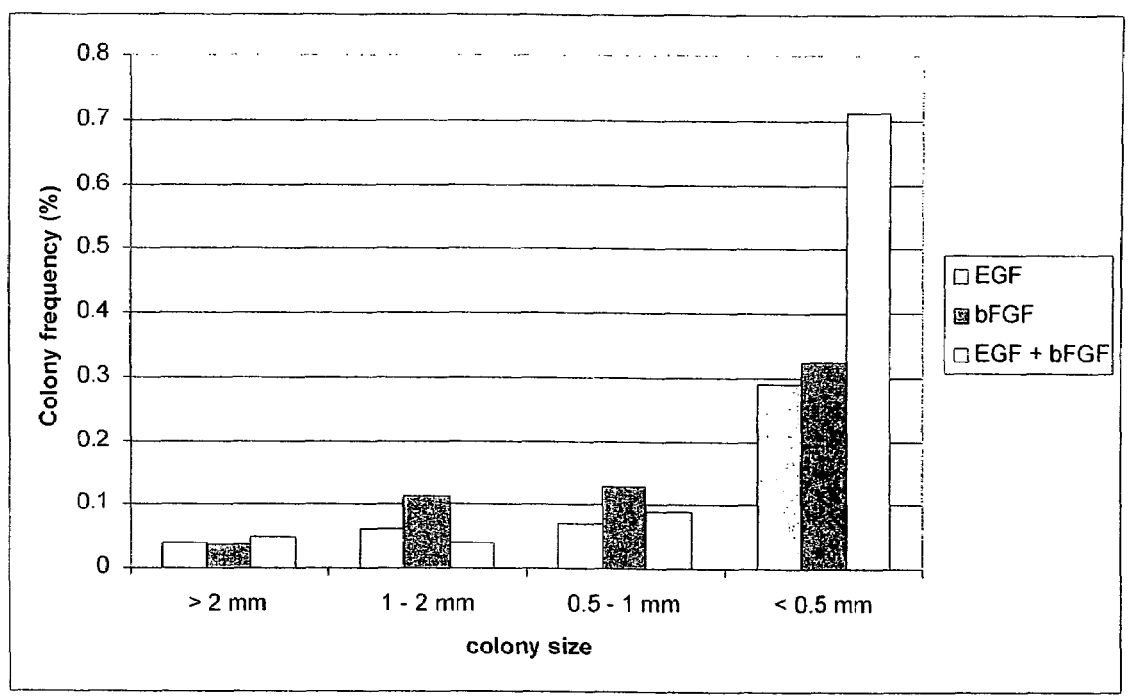

FIG. 27: The frequency (per total cells plated) of colonies generated by primary E14 mouse striatal cells in the NCFC assay supplemented with EGF, FGF or EGF plus FGF showing the colony size distribution.

Figure 28:
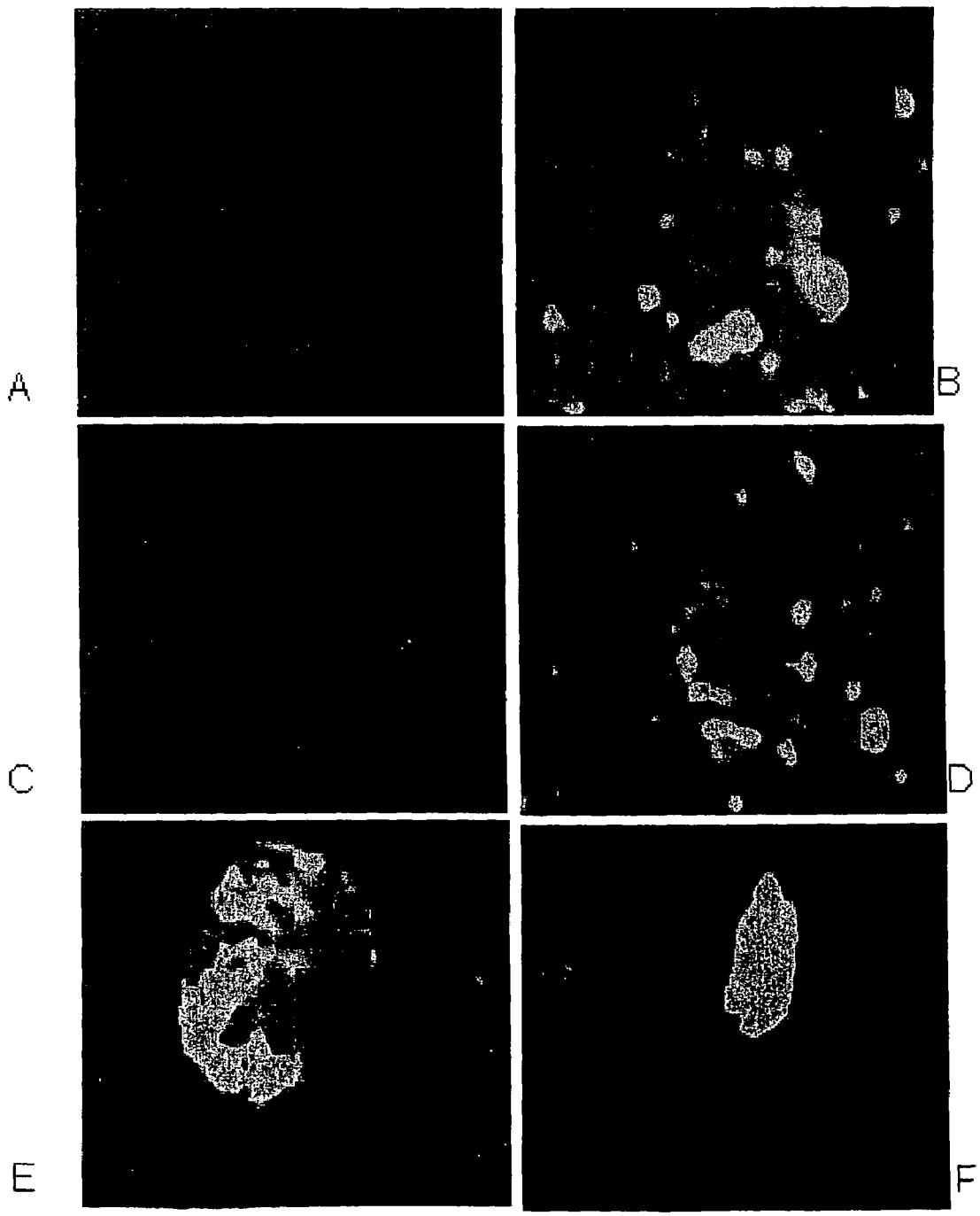

FIG. 28: In situ immunostaining of colonies generated from primary E14 mouse striatal cells in the NCFC assay. Staining of neuronal cells with an antibody against Beta-Tubulin shows B-Tubulin$^+$ cells in red within a colony >2 mm in diameter (A, B, colony is outlined), colony 1-2 mm in diameter (C, D), 0.5-1 mm in diameter (D) and <0.5 mm in diameter (E).

Figure 29:
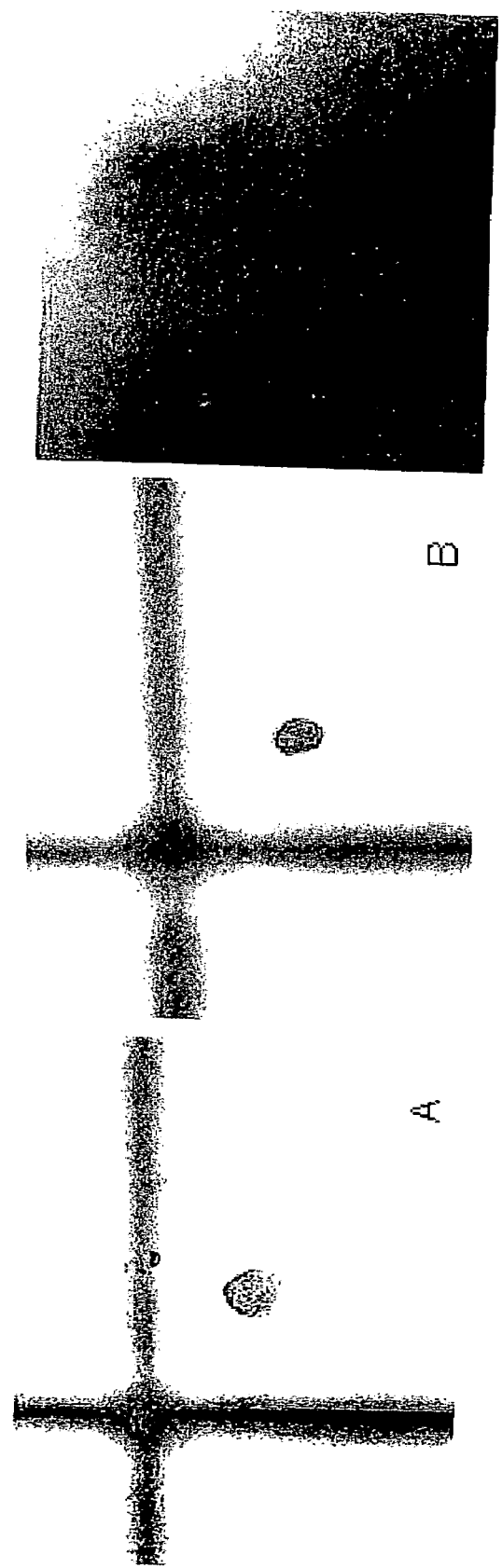

FIG. 29: Use of semi-solid methycellulose medium and cortical E14 mouse cells in the NCFC assay. Cortical E14 mouse cells formed colonies (A—10×, B—10×, C—40× magnification of B) in the NCFC assay containing methycellulose.

DETAILED DESCRIPTION OF THE INVENTION

The present invention provides methods for inducing the proliferation of NSC and progenitor cells derived from embryonic stem cells (ES), and embryonic, post-natal or adult CNS in a 3-D semi-solid medium. The invention allows for the distinction to be made between types of neural stem cells (NSC) and types of progenitor cells and to distinguish between different NSC based on their proliferative potential. In another aspect the invention allows for the distinction to be made between types of NSC and types of progenitor cells and to distinguish between different NSC and progenitor cells based on the morphology of the colonies they produce.

Detailed definitions of undifferentiated cells of the CNS can be found in U.S. Pat. No. 5,750,376. However, briefly, cells may be defined herein as:

Neural Progenitor Cell—undifferentiated cell that is not itself a stem cell. Neural progenitor cells have the capacity to proliferate and the capability to differentiate into more than one cell type. Neural progenitor cells can therefore be unipotent, bipotent or multipotent. A distinguishing feature of a neural progenitor cell is that, unlike a stem cell, it has a limited proliferative ability and does not exhibit self-maintenance.

Neural Stem Cell—as used herein, refers to an oligopotent or multipotent cell which is able to divide without limit and can produce daughter cells which terminally differentiate into neurons, astrocytes and oligodendrocytes. Neural stem cells are capable of self-maintenance and of generating a large number of progeny. The non-stem cell progeny of a neural stem cell are referred to as neural progenitor cells.

Precursor Cell—as used herein, refers to the progeny of neural stem cells and hence include both neural progenitor cells and neural stem cells.

The inappropriate use of these terms to identify undifferentiated cells in the CNS has led to confusion and misunderstanding in studying NSC and neural progenitor cells.

In one embodiment, the NSC can be distinguished from neural progenitor cells based on colony size. Accordingly, the present invention provides a method for identifying neural stem cells comprising:
    (a) suspending neural cells in a semi-solid medium which supports the growth of neural stem cells;
    (b) plating the cells in the semi-solid medium at a density that allows for the production of colonies;
    (c) culturing the plated cells until size differences can be discerned between the colonies; and
    (d) estimating colony size wherein the larger colonies are likely produced by neural stem cells.

The present invention also provides a method for identifying neural progenitor cells comprising:
    (a) suspending neural cells in a semi-solid medium which supports the growth of neural progenitor cells;
    (b) plating the cells in the semi-solid medium at a cell density that allows for the production of colonies;
    (c) culturing the plated cells until size differences can be discerned between the colonies; and
    (d) estimating colony size wherein the smaller colonies are likely produced by neural progenitor cells.

The neural cells can be from any suitable source. In a preferred embodiment, the neural cells are from primary CNS tissue or cultured neurospheres. The neural cells can be from any species of animal, preferably a mammal, more preferably a primate or rodent such as mice, rat or humans. The neural cells can be obtained from primary embryonic, post-natal or adult CNS tissue from any region of the neuroaxis including but not limited to the striatum, septum, cortex, ventral mesencephalon, septum, midbrain, cerebellum or spinal cord.

As an example, neural cells can be generated in the following manner. Striata or cortex are dissected from mouse embryos (e.g. day 14 embryos) using standard microdissection techniques. Tissue is collected in phosphate-buffered saline with 2% glucose then mechanically dissociated using a fire-polished glass pipette into a single cell suspension, washed once and filtered through a 40 μm nylon cell strainer (Falcon) and diluted to a concentration of about $8.0 \times 10^4$ cells/mL-$7.0 \times 10^5$ cells/mL, preferably about $2 \times 10^5$ cells per/mL in a suitable medium, preferably supplemented with EGF (e.g. 10-50 ng/ml, preferably 20 ng/ml EGF). Examples of suitable medium for neural stem cells include NeuroCult™ medium (NeuroCult™ Basal Medium & NeuroCult™ Proliferation Supplements; StemCell Technologies Inc.) and any medium comprised of a basal medium (for example MEM, DMEM/F12, Iscove's, McKoy's, RPMI), supplemented with glucose, HEPES and sodium bicarbonate; and a proliferation supplement consisting of components such as Insulin, Apotransferin, Progesterone, Putrescine, Sodium Selenite, Pituitary Extracts (O'Connor et al., 1996). In a preferred embodiment, the medium is serum free.

Alternately, cells from cultured neurospheres can also be used for the assay. Striata or cortex are dissected from mouse embryos using standard microdissection techniques. Tissue is collected in phosphate-buffered saline with 2% glucose then mechanically dissociated using a fire-polished glass pipette into a single cell suspension and plated in a suitable medium such as complete NeuroCult198 medium (NeuroCult™ Basal Medium & NeuroCult™ Proliferation Supplements; StemCell Technologies Inc.) with about 20 ng/ml of EGF. Cells are cultured for 7 days to generate neurospheres for use in the NCFC assay. Day 7 neurospheres are collected from the culture, mechanically dissociated into a single cell suspension, filtered through a 40 μm nylon cell strainer (Falcon) and diluted to a concentration of preferably about $2.0 \times 10^5$ cells per/mL in a suitable medium such as complete NeuroCult™ medium preferably containing a growth factor (e.g. EGF).

The neural cells are then suspended in a semi-solid medium. Any semi-solid medium that can support the growth of the cells can be used. Preferably the semi-solid medium is collagen-based or methycellulose-based (IMDM, DMEM/F12, McKoy's, Iscoves). The semi-solid medium may comprises the same suitable medium used to culture the neural cells (e.g. Neurocult™ serum free medium without cytokines; Neurocult™ Proliferation Supplements; and EGF) to which collagen or methylcellulose is added. In a preferred embodiment, the medium is serum free. Cells in the semi-solid medium are plated at a concentration that will allow sufficient number of colonies for statistical analyses of the data (e.g. 1000-25,000 cells, preferably 2500-7500 per 35 mm culture dish). The colonies which are formed arise from a single cell—either a neural stem cell or progenitor cell. The colonies are cultured until size and differences can be discerned between colonies sizes (e.g. about 10-30 days), colonies are counted and colony size is estimated using grids on a scoring dish. Colonies which were generated from a single neural stem cell will continue to grow in size over time, while colonies generated from a neural progenitor cell will have a limited ability to grow and hence not continue to grow in size over time. Colony size will distinguish between High Proliferative Potential—NSC (HPP-NSC), Low Proliferative Potential—NSC (LPP-NSC) and Neural Progenitors cells. Therefore, the size of the colony generated can be indicative of whether the colony was generated from a neural stem cell or neural progenitor cell and further whether the NSC have high or low proliferative potentials. In particular, the larger colonies (as compared to the other colonies on the dish) are indicative of high proliferative potential neural stem cells, mid-sized colonies are indicative of low proliferative potential neural progenitor cells, and the smaller colonies are indicative of neural progenitor cells. The actual diameter of the "larger colonies" or "smaller colonies" will depend on many factors, such as how long the colonies are cultured etc. For example, after culturing 2500 cells/dish for 14-28 days, colonies were classified into one of four categories based on diameter: (1) >2.0 mm, (2) 1-2 mm, (3) 0.5-1 mm and (4) <0.5 mm. Therefore, assuming the colonies are cultured for at least 14 days, a diameter of greater than 2.0 mm is indicative of a colony generated from a neural stem cell.

Cell types can also be distinguished based on morphologies they produce. Accordingly, the present invention provides a method for identifying neural stem cells comprising:

(a) suspending neural cells in a semi-solid medium which supports the growth of neural stem cells;
(b) plating the cells in the semi-solid medium at a density that allows for the production of colonies;
(c) culturing the plated cells until colonies are formed; and
(d) determining the morphology of the colonies wherein the presence of undulated colonies indicates that the colonies are produced by neural stem cells.

The present invention further provides a method for identifying neural progenitor cells comprising:
(a) suspending neural cells in a semi-solid medium which supports the growth of neural progenitor cells;
(b) plating the cells in the semi-solid medium at a density that allows for the production of colonies;
(c) culturing the plated cells until colonies are formed; and
(d) determining the morphology of the colonies wherein the presence of colonies with a smooth periphery indicates that the colonies are produced by neural progenitor cells.

In the above assays that detect NSC or neural progenitor cells based on morphology, the source of the neural cells as well as the assay media and conditions are as described above for the assay based on colony size.

As described in Example 6, the colonies of different sizes displayed different morphology. With respect to colonies >2 mm in diameter, in some cases the surface periphery of the colony contained protrusions and was undulated with a dense layer of cells below the protrusions. Other colonies >2 mm in diameter had varying degrees of cell density as reflected by the color intensity of the colonies. In some cases, the center of the large colony had a dark circle of cells. Different colony morphologies could also be observed for colonies 1-2 mm and 0.5-1 mm in diameter. The characteristics of the 1-2 mm colonies included hairy-like edges and dense central cores which are phase contrast dark. Other 1-2 mm colonies have a more homogenous cluster of cells. Some colonies 0.5-1 mm in diameter had a dense center and smooth surface while others had a star-like outer surface. Some colonies within this size range appeared very phase contrast dark and dense. The colony morphology observed for colonies <0.5 mm in diameter was not as distinct as those observed in the colonies from the other size categories. In some cases, a dense central core was observed in the <0.5 mm small colonies.

In another embodiment, the presence of neural stem cells can be assessed by determining antigen expression of the colonies. Accordingly, the present invention provides a method for identifying neural stem cells comprising:
(a) suspending neural cells in a semi-solid medium which supports the growth of neural stem cells;
(b) plating the cells in the semi-solid medium at a density that allows for the production of colonies;
(c) culturing the plated cells until colonies are formed; and
(d) determining the antigen expression of the colonies wherein the presence of markers associated with undifferentiated cells indicates that the colonies are produced by neural stem cells.

The present invention further provides a method for identifying neural progenitor cells comprising:
(a) suspending neural cells in a semi-solid medium which supports the growth of neural progenitor cells;
(b) plating the cells in the semi-solid medium at a density that allows for the production of colonies;
(c) culturing the plated cells until colonies are formed; and
(d) determining the antigen expression of the colonies wherein the presence of cell markers associated with specific neural lineages indicates that the colonies are produced by neural progenitor cells.

In the above assays that detect NSC or neural progenitor cells based on antigen expression, the source of the neural cells as well as the assay media and conditions are as described above for the assay based on colony size.

The antigen expression of the colonies can be determined by immunocytochemical staining by antibodies directed against markers for undifferentiated cells (eg anti-nestin, sox1, sox2, musashi, LexA, CD24) and differentiated cells (anti-Beta Tubulin, GFAP, O4, MAP2, MBP). One of skill in the art can readily determine other suitable markers. In one embodiment, the colonies are tested for nestin expression which is indicative of neural stem cells. In another embodiment, the colonies are tested for β-tubulin expression which is indicative of neural progenitor cells.

All of the above assays of the invention that distinguish between NSC and neural progenitor cells (e.g. based on size, morphology or antigen expression) can be collectively referred to herein as the Neural Colony Forming Cell (NCFC) assay, for ease of referral.

Given the ability of the NCFC assay to identify different NSC and to discriminate them from neural progenitor cells, the NCFC assay is useful for the screening of potential therapeutic compositions for efficacy (drugs targeted at specific subsets of NSC) or toxicity (drugs targeted to tissues/cells other than NSC). Desired compositions can be applied to the cultured cells at varying dosages and the response of the NSC or progenitor cells monitored. For instance, the effects of the composition on proliferation of NSC or neural progenitor cells can be determined, expression of new or increased levels of proteins such as enzymes, receptors, neurotransmitters and amino acids can be analyzed with any technique known in the art.

The NCFC assay can also be used to study the effects of in vivo manipulations of the CNS (genetic or epigenetic) and their effect on NSC and neural progenitor cells or the unintentional effects of compositions designed to treat non-CNS cells and the secondary or side effects that such compositions may have on NSC and neural progenitor cells. In this instance the animal would be treated with the composition, cells isolated from the CNS and the NCFC Assay used to evaluate the effects of the composition on proliferation, gene expression and or protein expression of NSC and neural progenitor cells.

Examples for the application of the NCFC assay can include drug screening, diagnostics of diseases and states of the CNS, detection of environmental effects on the CNS such as those caused by radiation, poisons, stimulating or environmental enrichment and evaluating animal models of CNS diseases.

Another application of the NCFC assay would be in screening for the effects of aging, dietary intake and exercise on the CNS.

The NCFC assay can be used in the research into the biology of neural stem cells and the identification of signals, growth factors, hormones, signal transduction molecules and neurotransmitters. For instance the use of NCFC assay can include research in the biology of neural development, biology of diseases of the CNS (Alzheimer's, Parkinson's, Multiple Sclerosis, cancer, brain tumor metastasis, tumor progression, Huntington's), biology of injuries in the CNS (spinal cord, recovery from surgery), biology of neurological syndromes (Schizophrenia) and the biology of aging and memory loss.

Other uses of the NCFC assay include of evaluating enhancement of brain function, perception of pain, post trauma healing, addictions, memory loss and behavioral disorders.

Diseases or disorders of the CNS such as neurodegenerative diseases (e.g. multiple sclerosis, Parkinson's disease, Alzheimer's disease, Amyotropic Lateral Sclerosis, Huntington's disease) and CNS injuries (e.g. stroke, head injury, spinal cord injury, cerebral palsy) involve the degeneration, malfunctioning, or loss of neural cells. It is expected that transplantation of neural stem cells may be used to treat such diseases or disorders of the CNS. Accordingly, the NCFC assay of the present invention can be used to assess the quality of the cell preparations that are used in therapy. The NSC identified according to the assay can also be used in the treatment of diseases or disorders of the CNS.

The following non-limiting examples are illustrative of the present invention:

EXAMPLES

Example 1

Neural Colony Forming Cell (NCFC) Assay Using Mouse Embryonic Day 14 Striatal Cells Neural cells can be obtained from primary embryonic, post-natal or adult CNS tissue from any region of the neuroaxis including but not limited to the striatum, septum, cortex, ventral mesencephalon, septum, midbrain, cerebellum or spinal cord from murine, rodent and human. Neural cells can also be obtained from cultured cells such as those generated using the Neurosphere Assay or any method known to one skilled in the art of neural tissue culture. Neural cells can also be obtained from any stage of embryonic stem cell cultures according to any standard procedure for culturing ES cells.

For example, striata and/or cortex are dissected from Embryonic Day 14 CD, albino mouse embryos (Charles River) using standard microdissection techniques. Tissue is collected in phosphate-buffered saline with 2% glucose then mechanically dissociated using a fire-polished glass pipette into a single cell suspension, washed once and filtered through a 40 µm nylon cell strainer (Falcon) and diluted to a concentration of $2.17 \times 10^5$ cells per/mL in complete NeuroCult™ medium (NeuroCult™ Basal Medium & NeuroCult™ Proliferation Supplements; StemCell Technologies Inc. with 20 ng/ml of EGF).

Alternately, cells from cultured neurospheres can also be used for the NCFC assay. Striata are dissected from Embryonic Day 14 $CD_1$ albino mouse embryos (Charles River) using standard microdissection techniques. Tissue is collected in phosphate-buffered saline with 2% glucose then mechanically dissociated using a fire-polished glass pipette into a single cell suspension and plated in a complete NeuroCult™ medium (NeuroCult™ Basal Medium & NeuroCult™ Proliferation Supplements; StemCell Technologies Inc.) with 20 ng/ml of EGF. Cells are cultured for 7 days to generate neurospheres for use in the NCFC assay. Day 7 neurospheres are collected from the culture, mechanically dissociated into a single cell suspension, filtered through a 40 µm nylon cell strainer (Falcon).

A single cell suspension of neural cells produced from either of the two examples mentioned above are diluted to a concentration of $2.17 \times 10^5$ cells per/ml in complete NeuroCult™ medium (StemCell Technologies Inc.). To make a 3.3 ml solution of the semi-solid NCFC assay media add the following components in the given order:

| | |
|---|---|
| NeuroCult ™ NCFC serum-free medium without cytokines (StemCell Technologies) | 1700 µl |
| NeuroCult ™ Proliferation Supplements (StemCell Technologies) | 330 µl |
| Epidermal Growth Factor (10 µg/ml) | 6.6 µl |
| Cells ($2 \times 10^5$ cell/ml) | 25 µl |
| Collagen (Bovine, StemCell Technologies) | 1300 µl |
| Total Volume | 3361 µl |

Mix the resulting solution well to evenly distribute the cells throughout the medium. 1.5 ml of the suspension is plated into individual 35 mm tissue culture plates at a final density of 2500 cells per dish. Cultures are placed in a tissue culture incubator set at 37° C., 100% humidity and 5% $CO_2$. The colonies are enumerated and sized number between day 14 -28.

Example 2

Growth of Neural Colonies Generated by Mouse Embryonic Day 14 Striatal Cells in Semi-Solid Culture (NCFC Assay) Versus Liquid Suspension Culture (Neurosphere Assay)

Cells were isolated from primary mouse CNS tissue or from day 7 cultures of neurospheres as detailed in Example 1 above. Briefly striata and/or cortex were dissected from Embryonic Day 14 $CD_1$ albino mouse embryos (Charles River) using standard microdissection techniques. Tissue was collected in phosphate-buffered saline with 2% glucose then mechanically dissociated using a fire-polished glass pipette into a single cell suspension, washed once and filtered through a 40 µm nylon cell strainer (Falcon) and diluted to a concentration of $2.17 \times 10^5$ cells per/mL in complete NeuroCult™ medium (NeuroCult™ Basal Medium & NeuroCult™ Proliferation Supplements; StemCell Technologies Inc. with 20 ng/ml of EGF).

Alternately, cells from cultured neurospheres can also be used for the NCFC assay as described previously. Striata are dissected from Embryonic Day 14 $CD_1$ albino mouse embryos (Charles River) using standard microdissection techniques. Tissue is collected in phosphate-buffered saline with 2% glucose then mechanically dissociated using a fire-polished glass pipette into a single cell suspension and plated in a complete NeuroCult™ medium (NeuroCult™ Basal Medium & NeuroCult™ Proliferation Supplements; StemCell Technologies Inc.) with 20 ng/ml of EGF. Cells are cultured for 7 days to generate neurospheres for use in the NCFC assay. Day 7 neurospheres are collected from the culture, mechanically dissociated into a single cell suspension, filtered through a 40 µm nylon cell strainer (Falcon).

A single cell suspension of neural cells produced from the two examples mentioned above are diluted to a concentration of $2.17 \times 10^5$ cells per/ml in complete NeuroCult™ medium (StemCell Technologies Inc.). To make a 3.3 ml solution of the semi-solid NCFC assay media add the following components in the given order:

| | |
|---|---|
| NeuroCult ™ NCFC serum-free medium without cytokines (StemCell Technologies) | 1700 µl |
| NeuroCult ™ Proliferation Supplements (StemCell Technologies) | 330 µl |

-continued

| Epidermal Growth Factor (10 µmg/ml) | 6.6 µl |
| Cells (2.17 × 10⁵ cell/ml) | 25 µl |
| Collagen (Bovine, StemCell Technologies) | 1300 µl |
| Total Volume | 3361 µl |

Mix the resulting solution well to evenly distribute the cells throughout the medium. 1.5 ml of the suspension is plated into individual 35 mm tissue culture plates at a final density of 2500 cells per dish. Cultures are placed in a tissue culture incubator set at 37° C., 100% humidity and 5% $CO_2$. Enumerate colony size and number between day 14-28.

Figure 1:
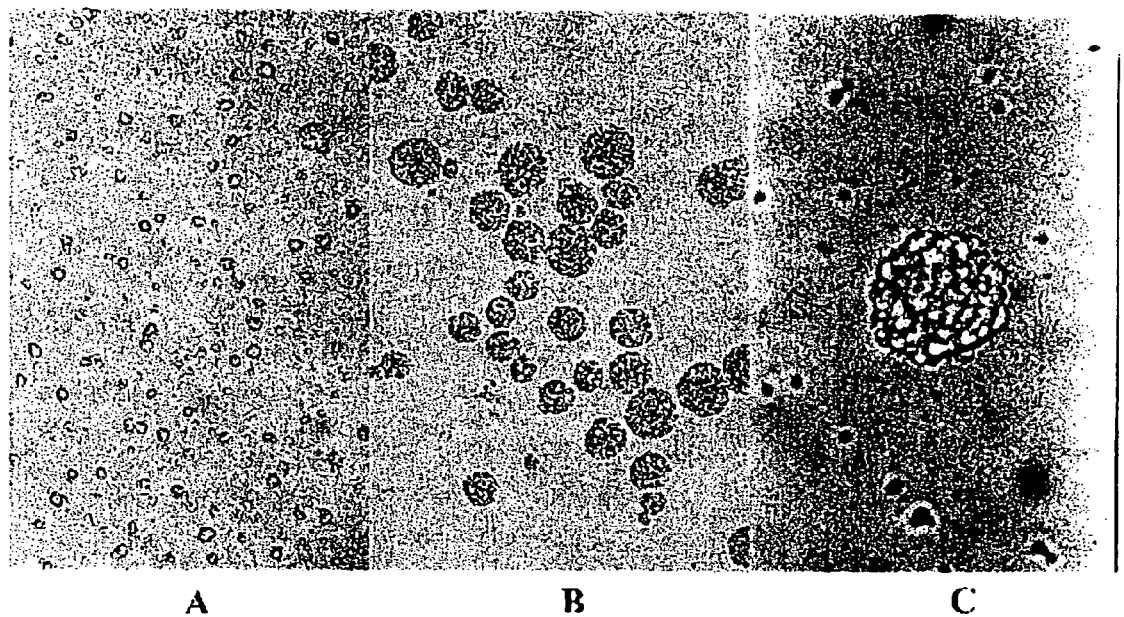
FIG. 1: First and Second Passage Neurosphere. Embryonic day 14 cortex was dissociated into a single cell suspension and plated in a defined serum-free medium containing EGF at a density of 500,000 cells per ml. Three days after plating small clusters of cells attached to the substrate can be identified (A). Four days later clonally derived neurospheres are seen floating in suspension (B). Neurospheres were collected, mechanically dissociated into a single cell suspension and replated. A second passage 7 day old neurosphere (C).
Figure 2:
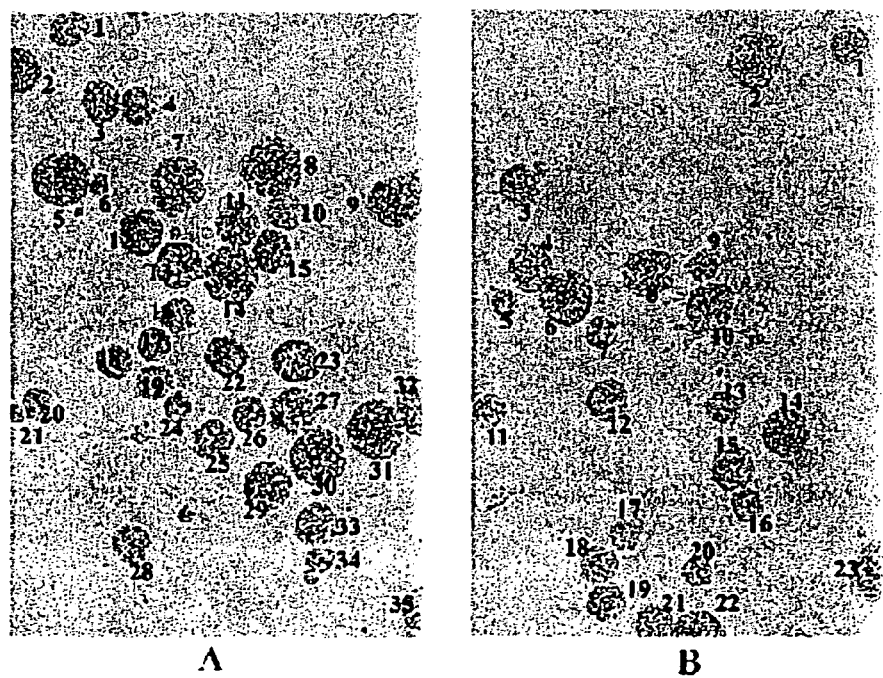
FIG. 2: Neurospheres Generated by mouse embryonic day 14 cortex in the Neurosphere Assay. Microphotographs of 7 day old neurospheres generated in the presence of EGF.
Figure 3:
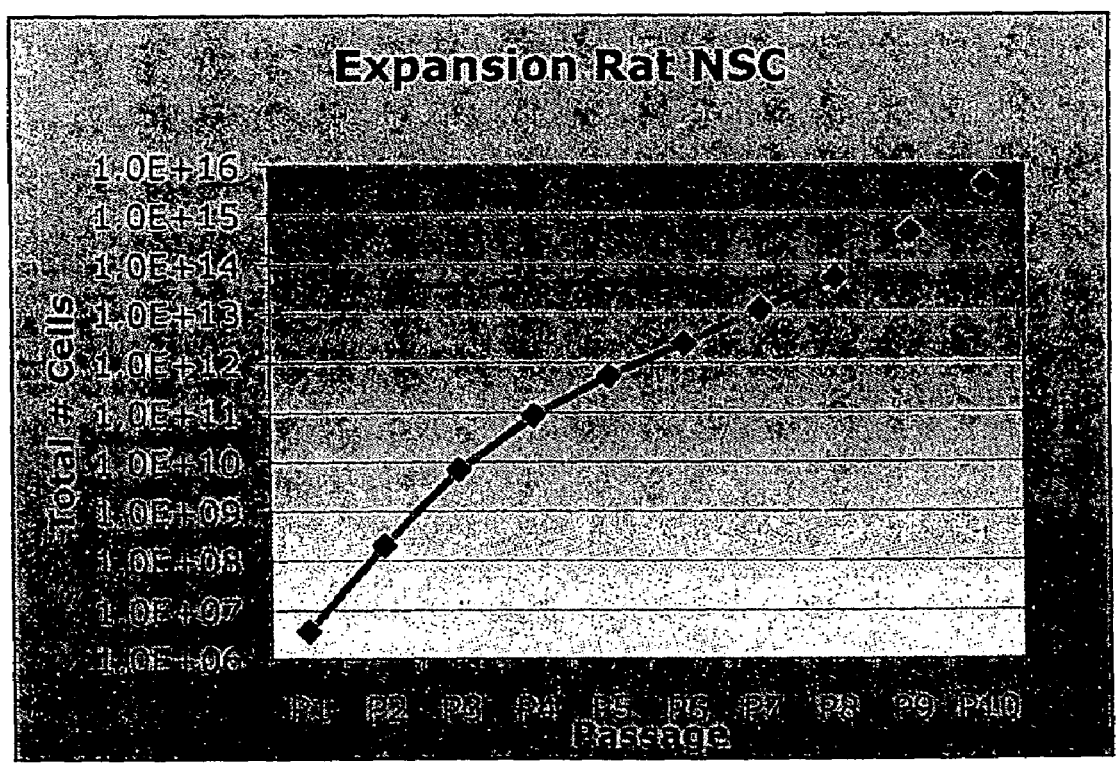
FIG. 3: Growth Curve of Passaged Rat E18 cortical NSC. Theoretical number of total viable cells generated after 10 passages. Data represent the potential total number of cells generated, based on aliquots counted at each passage, following 10 successive passages. Starting with $1 \times 10^6$ cells and had all the cells been saved at each passage, by passage 10, $4.03 \times 10^{15}$ cells would have been generated. This represents a $10^9$-fold increase over 10 weeks.
Figure 4:
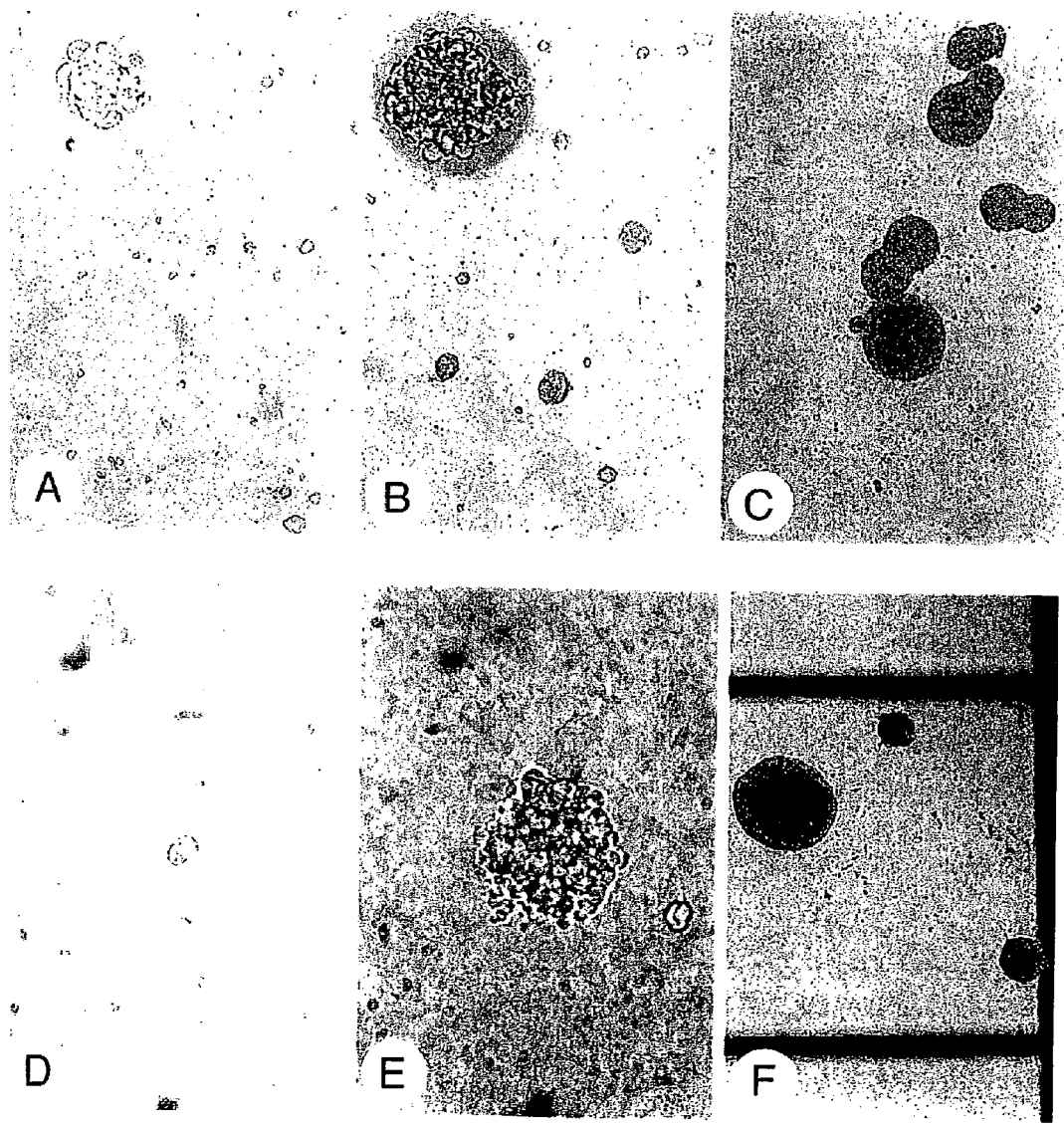
FIG. 4: Comparison of growth of colonies versus neurospheres generated from mouse embryonic day 14 striatal cells cultured in semi-solid collagen based medium (NCFC Assay) or liquid suspension cultures (Neurosphere Assay) respectively.

FIG. 4 shows the morphology of the neurospheres formed in a NCFC assay and Neurosphere Assay after the numbers of days in cultures as listed in the figure legend. FIG. 5 shows the number of colonies generated in the NCFC is similar to the number of colonies generated in the Neurosphere Assay. In summary, similar numbers of neurospheres and colonies are formed in the NA and NCFC Assay, respectively. This indicated that the culture conditions used in the NCFC Assay do not inhibit proliferation of EGF-responsive cells.

Example 3

Relationship Between Colony Size and Days in the NCFC Assay Using Mouse Embryonic Day 14 Striatal Cells Cells were isolated from primary mouse CNS tissue or from day 7 cultures of neurospheres as detailed in Example 1 above.

Within 4-7 days of plating in the NCFC assay NSC and neural progenitor cells begin to proliferate (FIG. 6A) forming small colonies. By 14 days these small colonies have grown in size and differences can be discerned between colonies (FIG. 6B). A number of the colonies appear to stop growing after approximately 10-14 days while other colonies continue to expand. By 21-28 days, colonies can be classified into at least 4 categories: 1) greater than 2 mm in diameter, 2) 1-2 mm in diameter, 3) 0.5 -1 mm in diameter and 4) less than 0.5 mm in diameter (FIG. 7).

Example 4

Sizes of Different Colony Types and Frequency of Colonies of the Various Sizes Generated in the NCFC Assay by Mouse Embryonic Day 14 Striatal Cells Colonies can be sized and counted and the frequency of colonies within each of these size categories graphed (FIG. 8A). This can also be expressed as a percentage of total cells plated (FIG. 8B) or as a percentage of total colonies generated (FIG. 8C). The majority (76%) of the colonies generated are less than 0.5 mm in size with a very small fraction (2.3%) forming large colonies grater than 2 mm in diameter.

Example 5

Proliferative Potential of Cells Dissociated from Colonies of Different Sizes Originally Generated from Mouse Embryonic Day 14 Striatal Cells within the Different Size Colonies The proliferative potential of the cell compromising the colonies of different sizes was measured by the following procedure. Colonies from the four size categories were isolated by cutting them from the collagen matrix and individually incubating them in a 0.25% solution of collagenase for 30 mins. at 37° C. (FIG. 9). The excised colony was then mechanically disrupted with a Gilson pipette tip, breaking up the matrix and producing a single cell suspension. All the cells from a single colony were plated into an individual well of a 24-well plated in complete NeuroCult™ medium supplemented with EGF (Neurosphere Assay). Ten to 14 days later, in wells where new spheres had formed, neurospheres were collected, mechanically dissociated and replated in fresh medium. This was repeated every 10-14 days. A HPP-NSC colony was excised from the NCFC assay as detailed above (FIG. 9). Under these culture conditions growth factor-responsive cell lines (FIGS. 10B-C and FIG. 11) were generated from colonies that were 2 mm or larger (HPP-NSC colony) in diameter but not in those that were less than 0.5 mm in diameter (FIG. 11).

Example 6

The Different Colony Morphologies Generated by Mouse Embryonic Day 14 Striatal Cells Cells were isolated from primary mouse CNS tissue or from day 7 cultures of neurospheres as detailed in Example 1 above.

Within 4-7 days of plating in the NCFC assay, NSC and neural progenitor cells begin to proliferate (FIG. 6A) forming small colonies. By 14 days these small colonies have grown to varying degrees and colonies of different sizes can be discerned (FIG. 6B). A number of the colonies appear to stop growing after approximately 10-14 days while other colonies continue to expand. By 21-28 days, colonies can be classified into at least 4 categories: 1) greater than 2 mm in diameter, 2) 1-2 mm in diameter, 3) 0.5-1 mm in diameter and 4) less than 0.5 mm in diameter (FIG. 7). Also by 21-28 days, differences in the colony morphologies within the various colony size categories can be observed. Colonies from the four size categories were photographed directly through the microscope and differences in morphologies recorded (FIGS. 13-16). These colonies from the four size categories were then isolated by cutting them from the collagen matrix and individually incubating them in a 0.25% solution of collagenase for 30 mins. at 37° C. (FIG. 9). The excised colony was then mechanically disrupted with a Gilson pipette tip, breaking up the matrix and producing a single cell suspension. All the cells from a single colony were plated into an individual well of a 24-well plated in complete NeuroCult™ medium supplemented with EGF (Neurosphere Assay). Ten to 14 days later, in wells where new spheres had formed, neurospheres were collected, mechanically dissociated and replated in fresh medium. This was repeated every 10-14 days. A HPP-NSC colony was excised from the NCFC assay as detailed above (FIG. 9). Under these culture conditions growth factor-responsive cell lines (FIGS. 10B-C) were generated from colonies that were 2 mm or larger (HPP-NSC colony) in diameter but not in those that were less than 0.5 mm in diameter.

The different colony morphologies observed for colonies of >2 mm in diameter is shown in FIG. 13. In some cases the surface periphery of the colony contained protrusions and was undulated with a dense layer of cells below the protrusions (FIG. 13A). Other colonies >2 mm in diameter had varying degrees of cell density as reflected by the color intensity of the colonies (FIGS. 13B and 13C). In some cases, the center of the large colony had a dark circle of cells (FIG. 13D).

Different colony morphologies could also be observed for colonies 1-2 mm and 0.5-1 mm in diameter (FIGS. 14 and 15). The characteristics of the 1-2 mm colonies included hairy-like edges (FIG. 14C) and dense central cores which are phase contrast dark (FIGS. 14A and 14B). Other 1-2 mm colonies have a more homogenous cluster of cells (FIG. 14D).

Some colonies 0.5-1 mm in diameter (FIG. 15) had a dense center and smooth surface (FIGS. 15A and 15B respectively) while others had a star-like outer surface (FIG. 15C). Some colonies within this size range appeared very phase contrast dark and dense (FIG. 15D).

The colony morphology observed for colonies <0.5 mm in diameter was not as distinct as those observed in the colonies from the other size categories (FIGS. 16A-D). In some cases, a dense central core was observed in the <0.5 mm small colonies (FIG. 16D).

As noted above, in the definition of NSC and neural progenitor cells, NSC have an extensive proliferative potential while neural progenitor cells have a limited proliferative potential. The ability of the large colonies to be passaged repeatably supports the conclusion that they were originally derived from a NSC. Alternatively, the inability of small colonies to exhibit continued proliferation and generate a large number of progeny supports that they are not stem cell derived but rather are neural progenitor cells. Therefore the NCFC assay was able to discriminate the cells with different proliferative potentials—high and low proliferative potentials.

Example 7

Neural Colony Forming Cell (NCFC)
Assay—Mouse Primary Embryonic Day 14 Striatal
CNS Tissue Neural cells were obtained from primary embryonic mouse CNS tissue from the region of the neuroaxis called the siriatum. For example, striata were dissected from Embryonic Day 14 $CD_1$ albino mouse embryos (Charles River) using standard microdissection techniques. Tissue was collected in phosphate-buffered saline with 2% glucose then mechanically dissociated using a fire-polished glass pipette into a single cell suspension, washed once and filtered through a 40 mm nylon cell strainer (Falcon) and diluted to a concentration of $2.17 \times 10^5$ cells per/mL in complete NeuroCult™ medium (NeuroCult™ Basal Medium & NeuroCult™ Proliferation Supplements; StemCell Technologies Inc. with 20 ng/ml of EGF).

A single cell suspension of neural cells produced from the example mentioned above was diluted to a concentration of $2.17 \times 10^5$ cells per/ml in complete NeuroCult™ medium (StemCell Technologies Inc.). To make a 3.3 ml solution of the semi-solid NSC assay media add the following components in the given order:

| | |
|---|---|
| NeuroCult NCFC serum-free medium without cytokines (StemCell Technologies) | 1700 μl |
| NeuroCult ™ Proliferation Supplements (StemCell Technologies) | 330 μl |
| Epidermal Growth Factor (10 μmg/ml) | 6.6 μl |
| Cells ($2.17 \times 10^5$ cell/ml) | 25 μl |
| Collagen (Bovine, StemCell Technologies) | 1300 μl |
| Total Volume | 3361 μl |

The resulting solution was mixed to evenly distribute the cells throughout the medium. 1.5 ml of the suspension was plated into individual 35 mm tissue culture plates at a final density of 2500 cells per dish. Cultures were placed in a tissue culture incubator set at 37° C., 100% humidity and 5% $CO_2$. The colonies were enumerated and sized number between day 14-28.

Example 8

Sizes of Different Colony Types and Frequency of Colonies of the Various Sizes Generated in the NCFC Assay Using Primary Mouse Embryonic Day 14 Striatal Cells Colonies were sized and counted and the frequency of colonies within each of these size categories summarized in Table 1. This result was expressed as a percentage of total cells plated (Table 1). Between 0.52 -1.1% of the total cells plated proliferated to varying degrees and formed different size colonies. A very small fraction (0.09%) of the total cells plated formed large (>2 mm) colonies. The majority of the colonies formed were<1 mm (0.5%) suggesting a more limited proliferative potential.

Example 9

Proliferative Potential of Primary Mouse Embryonic Day 14 Striatal Cells within Different Size Colonies The proliferative potential of the colonies of different sizes was measured by the following procedure. Colonies from the four size categories were isolated by cutting them from the collagen matrix and individually incubating them in a 0.25% solution of collagenase for 30 mins. at 37° C. (FIG. 9). The excised colony was then mechanically disrupted with a Gilson pipette tip, breaking up the matrix and producing a single cell suspension. All the cells from a single colony were plated into an individual well of a 24-well plated in complete NeuroCult™ medium supplemented with EGF (Neurosphere Assay). Ten to 14 days later, in wells where new spheres had formed, neurospheres were collected, mechanically dissociated and replated in fresh medium. This was repeated every 10-14 days. The cells from colonies >2 mm in diameter always generated secondary and tertiary neurospheres (FIG. 17). The cells from these tertiary neurospheres proliferated, expanded and maintained multi-lineage potential in long-term cultures, suggesting the original NCFC to be a NSC. Cells within colonies between 1-2, 0.5-1 and those less than 0.5 mm produced secondary spheres 50, 36 and 17 percent of the time, respectively. The cells from colonies 1-2 mm in diameter generated tertiary spheres 8.3% of the time, however these could not be passaged. Cells from colonies <1 mm in diameter never produced tertiary spheres suggesting that the original NCFCs did not have all the characteristics of NSC described in the background and were progenitors.

Example 10

Multi-Lineage Differentiation Potential of Secondary Spheres Generated from Colonies >2 mm from Primary Mouse Embryonic Day 14 Striatal Cells The multi-lineage differentiation potential of the colonies greater than 2 mm was measured by the following procedure. Individual colonies >2 mm were isolated by cutting them from the collagen matrix and individually incubating them in a 0.25% solution of collagenase for 30 mins. at 37° C.

(Method diagram in FIG. 9). The excised colony was then mechanically disrupted with a Gilson pipette tip, breaking up the matrix and producing a single cell suspension. All the cells from a single colony were plated into an individual well of a 24-well plated in complete NeuroCult™ medium supplemented with EGF (Neurosphere Assay). Ten to 14 days later, in wells where new spheres had formed, neurospheres were collected, mechanically dissociated and all cells from the colony plated in pre-coated poly-D-Lysine/Laminin #35-4688 Becton Dickinson BioCoat 8-well Culture Slides containing 0.8 mL of complete NeuroCult™ medium supplemented with 1% serum. Under these culture conditions the cells differentiated and were then further processed for immunostaining using the following procedure. Cultures are observed after 6-8 days with an inverted light microscope to determine if cells have differentiated and are viable. The medium was changed during the differentiation procedure, depending on the number of cells plated and if the medium became acidic (turns yellow/orange in colour). The medium was changed by removing approximately 50% of the medium and replacing with fresh complete NeuroCult™ medium supplemented with 1% serum.

After 10 days of culture the culture medium was removed from each chamber containing differentiating cells (taking care not to remove all the medium and exposed the unfixed cells to air) and 1 mL of the 4% para-formaldehyde solution was added directly into the chamber. Cells were incubated for 30 minutes at room temperature. The para-formaldehyde solution was aspirated using an aspiration system connecting to a vacuum pump. PBS (pH 7.2) was added to the samples and incubate for 5 minutes. This washing procedure was repeated for two more times for a total of 3 wash steps. Next, the cells were permeabilized by adding 1 mL of PBS containing 0.3% Triton X-100 to each well and incubating for 5 minutes at room temperature. After 5 minutes the PBS/Triton-X 100 was removed by aspiration and two 5 min. PBS washes were performed.

The samples were then labeled with primary antibodies directed against the specific lineage markers Beta-Tubulin for neurons, GFAP for astrocytes and O4 for oligodendrocytes. The primary antibodies were diluted at the optimal working dilutions (Beta-Tubulin antibody used at 1:1000; GFAP antibody used at 1:100 and O4 antibody used at 1:50) in the diluent solution PBS containing 10% goat serum. A 250 µL volume of the diluted antibodies was then added directly into the chamber and all samples were incubated for 2 hours at 37° C. After the incubation period, the primary antibody was washed off with three 5 minute washes using PBS. Next, the secondary antibodies, goat anti-mouse IgG (H+L) Texas Red dye-conjugated, goat anti-rabbit IgG (H+L) AMCA-conjugated and goat ant-mouse IgM, µ chain specific FITC-conjugated were diluted in PBS containing 2% serum (same serum used as diluent for the primary antibody), and added to each chamber slide. The samples were incubated with 250 µL of the secondary antibodies for 30 minutes at 37° C. After the incubation, the secondary antibodies were washed off with three 5 minute washes using PBS. The chamber was removed from the glass slides by following the manufacturer's protocol. 5 µL of mounting medium was added in each chamber slot which was then covered with a 75 mm coverslip avoiding trapping any air bubbles. The immunfluorescence was visualized under a fluorescent microscope using the appropriate filters for each fluorophore.

Cells isolated from secondary spheres originally generated from colonies >2 mm were able to produce the three cell phenotypes found in the CNS—neurons, astrocytes and oligodendrocytes (FIG. 18) suggested that the original NCFCs to be a NSC.

Example 11

In situ Immunostaining of Colonies Generated by Primary Mouse Embryonic Day 14 Striatal Cells in the NCFC Assay The colonies formed in the NCFC assay can also be immunocytochemically stained directly in situ since the collagen gels can be dried and stained. Growth, dehydration, fixation and staining of the neural colonies are all performed on 35 mm culture dishes and over-sized (75 mm×50 mm) slides. In situ staining of colonies in the NCFC assay was performed according to the following procedure. A container containing approximately 200 mL of acetone was placed on ice for a minimum of 15 minutes. The 35 mm culture dishes used in the NCFC assay was removed from the incubator and the lids from dishes removed. Each culture dish containing the collagen gel and embedded colonies was flipped upside down onto an over-sized 75 mm×50 mm slide. A pre-cut polypropylene separator was placed onto the collagen gel together with a thick white filter card to allow liquid to soak the card. The thick white card was then removed leaving the original polypropylene separator in place. The entire slides containing the collagen gel and spacers was placed horizontally into an appropriate plastic container filled with about 200 mL of cold acetone. The polypropylene spacers floated off, leaving the collagen gel on the slide. The slides were left in acetone for five minutes. The slides were removed from the fixative and allowed to air dry, vertically. The glass slides were placed in a plastic container containing 4% para-formaldehyde and samples incubated for 30 minutes at room temperature. The para-formaldehyde solution was poured off and approximately 20 mL of PBS (pH 7.2) was added to the samples and incubate for 5 minutes. This washing procedure was repeated for two more times for a total of 3 wash steps. Next, the cells were permeabilized by adding 20 mL of PBS containing 0.3% Triton X-100 into the plastic container containing the glass slide and samples incubated for 5 minutes at room temperature. After 5 minutes the PBS/Triton-X 100 was poured off and two 5 minute PBS washes were performed.

The samples were then labeled with the primary antibody directed against nestin, a marker for undifferentiated neural cells. The anti-nestin antibody was diluted at 1:50 in PBS containing 10% goat serum. Approximate 500 µL of the diluted antibody was then added directly onto the dehydrated collagen gel on the glass slide and a piece of parafilm was placed on top of the antibody solution. All samples were incubated for 2 hours at 37° C. After the incubation period, the primary antibody was washed off with three 5-minute washes using PBS. Next, the secondary antibody, goat anti-mouse IgG (H+L) Texas Red-conjugated was diluted in PBS containing 2% goat serum, and added directly to the dehydrated collagen gel on the to glass slide. A piece of parafilm was placed on top of the antibody solution and the samples were incubated with the secondary antibodies for 30 minutes at 37° C. After the incubation, the secondary antibodies were washed off with three 5-minute washes using PBS. 5 µL of mounting medium was added in the middle of the each dehydrated collagen gel and then covered with a coverslip avoiding trapping any air bubbles. The immunfluorescence was visualized under a fluorescent microscope using the appropriate filters for each fluorophore.

Cells within colonies >2 mm were highly positive for nestin expression and the majority of cells within these colonies stained for nestin (FIG. 19A). Colonies 1-2 mm (FIG. 19B) and 0.5-1 mm in diameter (FIG. 19C) contained lower numbers of cells which were positive for nestin expression compared to cells within colonies >2 mm in diameter while colonies <0.5 mm contained the lowest numbers of nestin positive cells (FIG. 19D). This indicated that colonies >2 mm contained higher numbers of undifferentiated cells which would include NSC and progenitors compared to colonies <2 mm in diameter.

Example 12

Neural Colony Forming Cell (NCFC) Assay Using Increased Mouse Primary Embryonic Day 14 Striatal Cell Numbers Neural cells were obtained from primary embryonic mouse CNS tissue from the region of the neuroaxis called the striatum. For example, striata were dissected from Embryonic Day 14 $CD_1$ albino mouse embryos (Charles River) using standard microdissection techniques. Tissue was collected in phosphate-buffered saline with 2% glucose then mechanically dissociated using a fire-polished glass pipette into a single cell suspension, washed once and filtered through a 40 μm nylon cell strainer (Falcon) and diluted to a concentration of $6.51 \times 10^5$ cells per/mL in complete NeuroCult™ medium (NeuroCult™ Basal Medium & NeuroCult™ Proliferation Supplements; StemCell Technologies Inc. with 20 ng/ml of EGF). This concentration of cells is three times higher than that used for passaged 2 E14 striatal neurospheres in Example 1 and primary striatal cells in Example 7 ($2.17 \times 10^5$ cells/mL). The concentration of $6.51 \times 10^5$ cells/mL yields 7500 total cells plated per 35 mm dish, which was found to be produce the appropriate numbers of colonies for scoring.

A single cell suspension of neural cells produced from the example mentioned above was diluted to a concentration of $6.51 \times 10^5$ cells per/ml in complete NeuroCult™ medium (StemCell Technologies Inc.). To make a 3.3 ml solution of the semi-solid NSC assay media add the following components in the given order:

| | |
|---|---|
| NeuroCult NCFC serum-free medium without cytokines (StemCell Technologies) | 1700 μl |
| NeuroCult ™ Proliferation Supplements (StemCell Technologies) | 330 μl |
| Epidermal Growth Factor (10 μmg/ml) | 6.6 μl |
| Cells ($2.17 \times 10^5$ cell/ml) | 25 μl |
| Collagen (Bovine, StemCell Technologies) | 1300 μl |
| Total Volume | 3361 μl |

The resulting solution was mixed to evenly distribute the cells throughout the medium. 1.5 ml of the suspension was plated into individual 35 mm tissue culture plates at a final density of 7500 cells per dish. Cultures were placed in a tissue culture incubator set at 37° C., 100% humidity and 5% $CO_2$. The colonies were enumerated and sized number between day 14-28.

Example 13

Figure 20B:
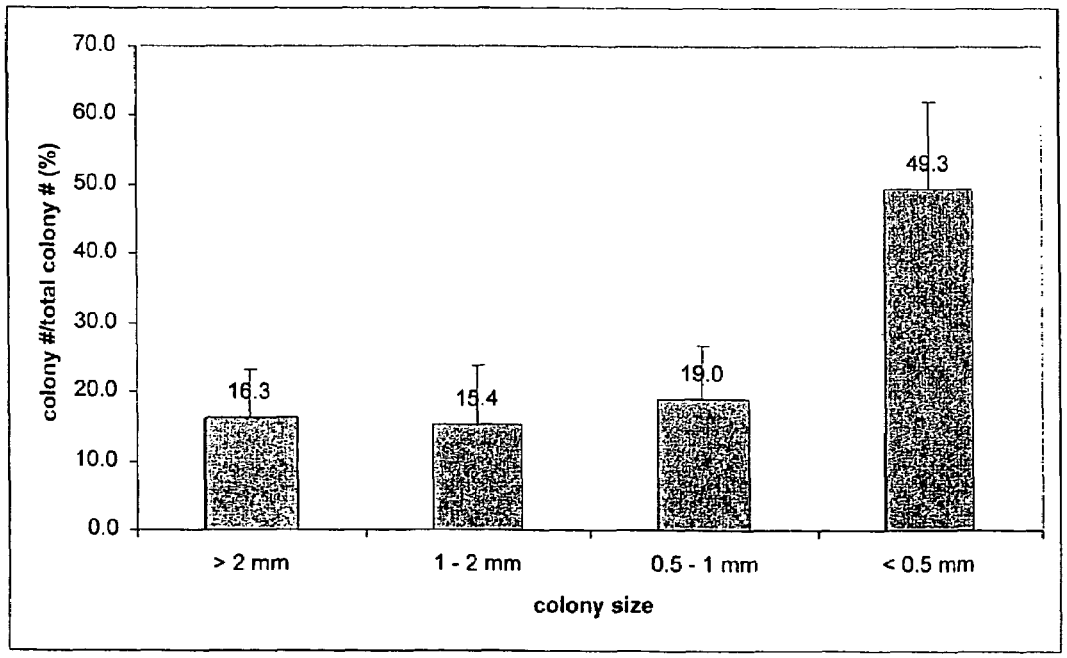
Figure 20C:
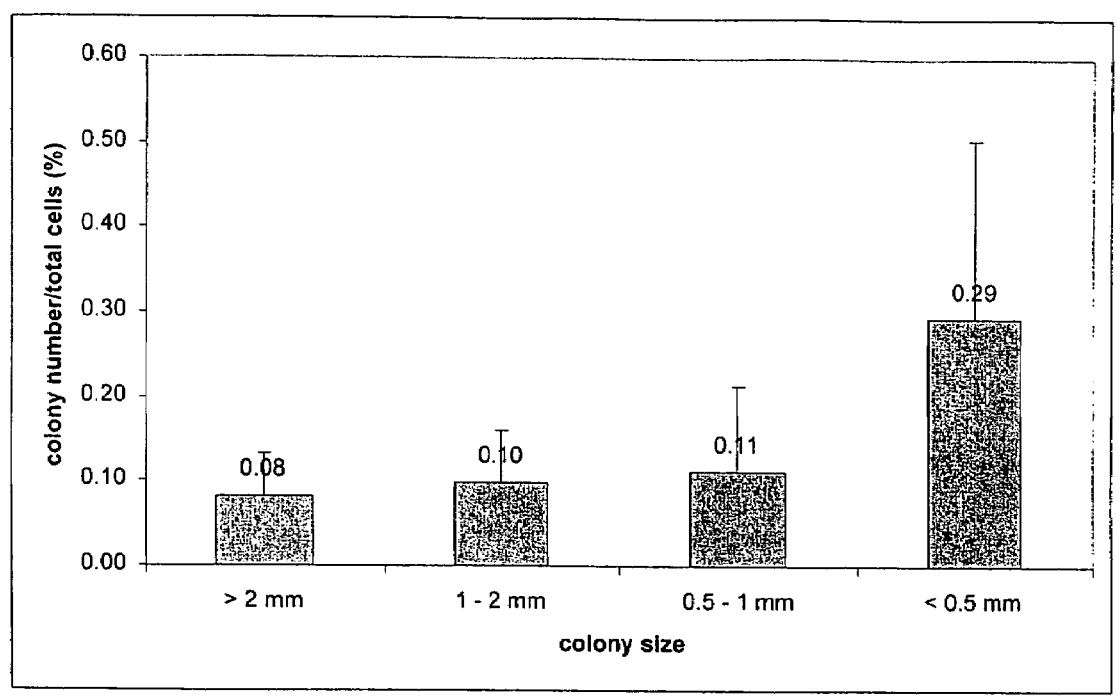

Sizes of Different Colony Types and Frequency of Colonies of the Various Sizes Generated in the NCFC Assay—Mouse Primary Embryonic Day 14 Striatal CNS Tissue Cells from primary embryonic CNS tissue were cultured in the NCFC assay as described in Example 12. Colonies were be sized and counted and the frequency of colonies within each of these size categories graphed (FIG. 20). This was expressed as a percentage of total cells plated (FIG. 20C) or as a percentage of total colonies generated (FIG. 20B). The majority (50%) of the colonies generated are less than 0.5 mm in size with a 16% forming large colonies grater than 2 mm in diameter. A very small fraction (0.08%) of the total cells plated formed large (>2 mm) colonies. The majority of the colonies formed were <1 mm (0.4%) suggesting a more limited proliferative potential.

Example 14

Sizes of Different Colony Types and Frequency of Colonies of the Various Sizes Generated by Cells from Colonies >2 mm in Diameter Re-Plated in the NCFC Assay—Mouse Primary Embryonic day 14 Striatal CNS Tissue Cells from primary embryonic CNS tissue were cultured in the NCFC assay as described in Example 12. The ability of cells within colonies >2 mm in diameter to generate the different colony types when re-plated back into the NCFC was measured by the following procedure. Colonies >2 mm in diameter were isolated by cutting them from the collagen matrix and individually incubating them in a 0.25% solution of collagenase for 30 mins. at 37+ C. (FIG. 9). The excised colony was then mechanically disrupted with a Gilson pipette tip, breaking up the matrix and producing a single cell suspension. All the cells from a single colony were plated into an individual well of a 96-well plated in complete NeuroCult™ medium supplemented with EGF (Neurosphere Assay). Ten to 14 days later, in wells where new spheres had formed (secondary spheres), neurospheres were collected, mechanically dissociated and replated in fresh medium in a 24-well plate to generate tertiary spheres. Ten to 14 days later, in wells where tertiary neurospheres had formed, neurospheres were collected, mechanically dissociated and viable cells counted using Trypan blue exclusion. Cells were then plated in the NCFC assay according to the procedure below. The concentration of cells was adjusted to $2.17 \times 10^5$ cells per/mL in complete NeuroCult™ medium (NeuroCult™ Basal Medium & NeuroCult™ Proliferation Supplements; StemCell Technologies Inc. with 20 ng/ml of EGF) and added to the semi-solid NCFC assay media in the given order:

| | |
|---|---|
| NeuroCult ™ NCFC serum-free medium without cytokines (StemCell Technologies) | 1700 μl |
| NeuroCult ™ Proliferation Supplements (StemCell Technologies) | 330 μl |
| Epidermal Growth Factor (10 μmg/ml) | 6.6 μl |
| Cells | 25 μl |
| Collagen (Bovine, StemCell Technologies) | 1300 μl |
| Total Volume | 3361 μl |

The resulting solution was mixed to evenly distribute the cells throughout the medium. 1.5 ml of the suspension was plated into individual 35 mm tissue culture plates at a final density of 2500 cells per dish. Cultures were placed in a tissue culture incubator set at 37° C., 100% humidity and 5% $CO_2$. The colonies were enumerated and sized number between day 14-28. Cells within colonies >2 mm in diameter were able to re-generate colonies of the different size categories (FIG. 21).

Example 15

Long Term Proliferative Potential and Expansion of Cells from Colonies >2 mm in Diameter—Mouse Primary Embryonic Day 14 Striatal CNS Tissue Cells from primary embryonic CNS tissue were cultured in the NCFC assay as described in Example 12. The ability of cells within colonies >2 mm in diameter to self-renew and generate a large number of progeny in long-term neurosphere cultures (beyond tertiary neurospheres) was measured by the following procedure. Colonies >2 mm in diameter were isolated by cutting them from the collagen matrix and individually incubating them in a 0.25% solution of collagenase for 30 mins. at 37° C. (FIG. 9). The excised colony was then mechanically disrupted with a Gilson pipette tip, breaking up the matrix and producing a single cell suspension. All the cells from a single colony were plated into an individual well of a 96-well plated in complete NeuroCult™ medium supplemented with EGF (Neurosphere Assay). Ten to 14 days later, in wells where new spheres had formed (secondary spheres), neurospheres were collected, mechanically dissociated and replated in fresh medium in a 24-well plate to generate tertiary spheres. Ten to 14 days later, in wells where tertiary neurospheres had formed, neurospheres were collected, mechanically dissociated and cells plated in 6-well plates containing complete NeuroCult™ medium supplemented with EGF. Ten to 14 days later, in wells where neurospheres had formed, neurospheres were collected, mechanically dissociated and viable cells counted using Trypan blue exclusion. All cells were then plated in a T-25 $cm^2$ flask containing complete NeuroCult™ medium supplemented with EGF (Passage 4). This re-plating process was repeated every 10-14 days to generate long-term cultures. At each culture passage cell numbers were counted and the fold expansion was calculated by dividing the total number of viable cells at each passage with the total number of viable cells seeded at that passage. The cumulative fold expansion (passage 6-10) in total number of viable cells was then calculated from the starting cell number at passage 6 (FIG. 22). Cells from four individual colonies >2 mm in diameter showed increasing fold expansion in total numbers of viable cells however the growth rate of the cells varied. Cells from colonies >2 mm in diameter were able to self-renew beyond 8 passages and produce increasing numbers of progeny, two important features of a neural stem cell.

Example 16

Neural Colony Forming Cell (NCFC) Assay Using Primary Embryonic Day 18 (E18) Rat Cortical Cells Neural cells can be obtained from primary embryonic, post-natal or adult CNS tissue from any region of the neuroaxis including but not limited to the striatum, septum, cortex, ventral mesencephalon, septum, midbrain, cerebellum or spinal cord from murine, rodent and human.

Cortices were dissected from Embryonic Day 18 Sprague-Fischer 344 rat embryos (BrainBits, Ill., USA) using standard microdissection techniques. Tissue is collected in phosphate-buffered saline with 2% glucose then mechanically dissociated using a p200 Gilson pipette with a plastic disposable pipette tip into a single cell suspension, washed once and filtered through a 40 µm nylon cell strainer (Falcon) and diluted to a concentration of $6.51 \times 10^5$ cells per/mL in complete NeuroCult™ medium (NeuroCult™ NS-A Basal Medium & NeuroCult™ Proliferation Supplements; StemCell Technologies Inc. with 20 ng/ml of EGF, 10 ng/mL basic fibroblast growth factor—bFGF and 2 ng/mL heparin).

A 3.3 ml solution of the semi-solid NSC assay media was obtained by adding the following components in the given order:

| | |
|---|---:|
| NeuroCult ™ NCFC serum-free medium without cytokines (StemCell Technologies) | 1700 µl |
| NeuroCult ™ Proliferation Supplements (StemCell Technologies) | 330 µl |
| Epidermal Growth Factor (10 µg/ml) | 6.6 µl |
| Basic Fibroblast Growth Factor (10 µg/ml) | 3.3 µl |
| Heparin Solution (0.2%) | 6.6 µl |
| Cells ($6.51 \times 10^5$ cell/ml) | 25 µl |
| Collagen (Bovine, StemCell Technologies) | 1300 µl |
| Total Volume | 3361 µl |

The resulting solution was mixed well to evenly distribute the cells throughout the medium. 1.5 ml of the suspension was plated into individual 35 mm tissue culture plates at a final density of 7500 cells per dish. Cultures are placed in a tissue culture incubator set at 37° C. 100% humidity and 5% $CO_2$. The colonies are enumerated and sized number between day 14-28 (FIG. 23).

Example 17

Relationship Between Colony Size and Days in the NCFC Assay of Primary E18 Rat Cortical Cells Cells were isolated from primary E18 rat cortex CNS tissue and cultured in the NCFC assay as detailed in Example 16 above. By 21-28 days, colonies can be classified into at least 4 categories: 1) greater than 2 mm in diameter, 2) 1-2 mm in diameter, 3) 0.5-1 mm in diameter and 4) less than 0.5 mm in diameter. FIG. 23 shows two E18 rat colonies 1-2 mm in diameter observed in the NCFC assay.

Example 18

Figure 24B:
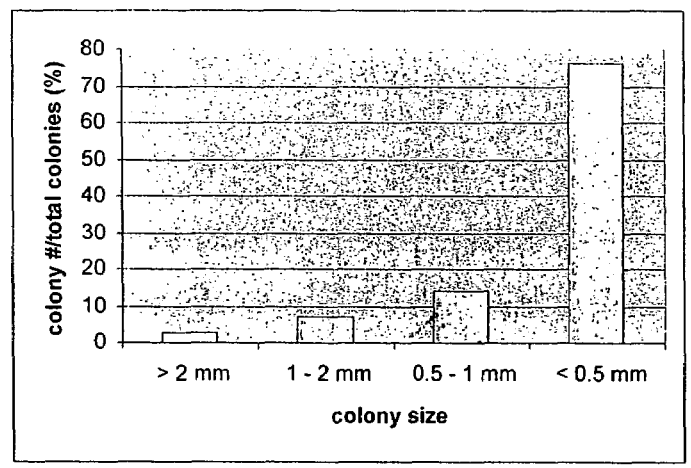
Figure 24C:
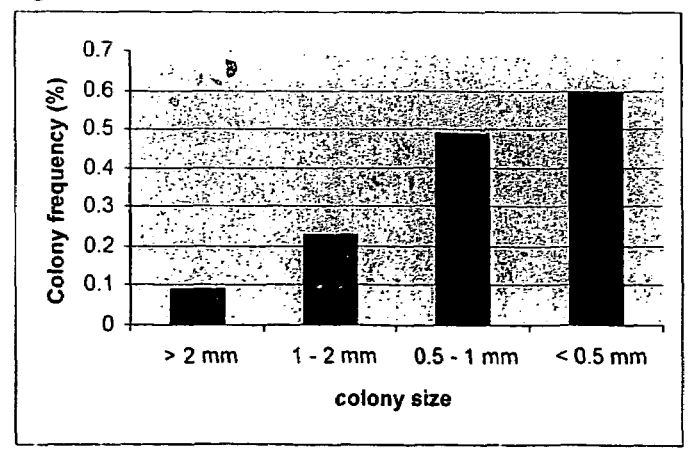

Sizes of Different Colony Types and Frequency of Colonies of the Various Sizes Generated in the NCFC Assay Using Primary E18 Rat Cortical Cells Colonies can be sized and counted and the frequency of colonies within each of these size categories graphed (FIGS. 24 A-C). This can also be expressed as a percentage of total cells plated (FIG. 24C) or as a percentage of total colonies generated (FIG. 24B). The majority (77%) of the colonies generated are less than 0.5 mm in size with a very small fraction (0.2%) forming large colonies greater than 2 mm in diameter.

Example 19

Neural Colony Forming Cell (NCFC) Assay Using Primary Adult Subventricular Zone (SVZ) Mouse Cells Neural cells can be obtained from the adult mouse CNS tissue from a region of the neuroaxis called the subventricular zone (SVZ) which harbors proliferating neural stem and progenitor cells. For example, the SVZ region was dissected from 6 adult $CD_1$ albino mice (Charles River) using standard microdissection techniques. Tissue is collected in phosphate-buffered saline with 2% glucose, minced with a scalpel and then enzymatically treated with a Trypsin and DNAse solution for 15 mins. at 37° C. After the 15 mins incubation, Ovomucoid Trypsin inhibitor was added to the cells and mixed gently. The cell suspension was centrifuged for 5 mins. at 800 rpm and the supernatant was discarded. The cell pellet was resuspended in 150 μL of complete NeuroCult™ medium (NeuroCult™ NS-A Basal Medium & NeuroCult™ Proliferation Supplements; StemCell Technologies Inc. with 20 ng/ml of EGF, 10 ng/mL basic fibroblast growth factor—bFGF and 2 μg/mL heparin) and mechanically dissociated using a p200 Gilson pipette with a plastic disposable pipette tip into a single cell suspension. The cell suspension was washed two more times (centrifugation) and the final pellet resuspended in 1 mL of complete NeuroCult™ medium (NeuroCult™ NS-A Basal Medium & NeuroCult™ Proliferation Supplements; StemCell Technologies Inc. with 20 ng/ml of EGF, 10 ng/mL basic fibroblast growth factor—bFGF and 2 μg/mL heparin) and filtered through a 40 μm nylon cell strainer (Falcon). It is extremely difficult to count adult mouse cells due to contamination with cell debris, myelin and other cell types, therefore cell counts are not reliable. One hundred and fifty microliters (150 μL) from the final 1 mL cell suspension is used in the NCFC assay. The semi-solid NSC assay media was obtained by adding the following components in the given order:

| | |
|---|---|
| NeuroCult ™ NCFC serum-free medium without cytokines (StemCell Technologies) | 1700 μl |
| NeuroCult ™ Proliferation Supplements (StemCell Technologies) | 330 μl |
| Epidermal Growth Factor (10 μg/ml) | 6.6 μl |
| Basic Fibroblast Growth Factor (10 μg/ml) | 3.3 μl |
| Heparin Solution (0.2%) | 6.6 μl |
| Adult SVZ Cells (6 brains in 1 mL) | 150 μl |
| Collagen (Bovine, StemCell Technologies) | 1300 μl |
| Total Volume | 3361 μl |

The resulting solution was mixed well to evenly distribute the cells throughout the medium. 1.5 ml of the suspension was plated into four individual 35 mm tissue culture plates. Cultures are placed in a tissue culture incubator set at 37° C. 100% humidity and 5% $CO_2$. The colonies are enumerated and sized number between day 14-28 (FIG. 25).

Example 20

Adult Subventricular Zone (SVZ) Mouse Neural Colony Forming Cells (NCFC)

Cells were isolated from adult SVZ cells from the mouse CNS tissue and cultured in the NCFC assay as detailed in Example 19 above. By 21-28 days, colonies can be classified into at least 4 categories: 1) greater than 2 mm in diameter, 2) 1-2 mm in diameter, 3) 0.5-1 mm in diameter and 4) less than 0.5 mm in diameter (FIG. 25).

Example 21

Neural Colony Forming Cell (NCFC) Assay Using Passaged 4 Neurospheres from Fetal Human Cortical Cells Neural cells can be obtained from primary embryonic, post-natal or adult CNS tissue from any region of the neuroaxis including but not limited to the striatum, septum, cortex, ventral mesencephalon, septum, midbrain, cerebellum or spinal cord from murine, rodent and human.

Cells from passage 4 human neurospheres were used for the NCFC assay (Refer to Method). Briefly, passage 4 neurospheres were centrifuged for 5 mins. At 400 rpm abd the supernatant was discarded. The cell pellet was resuspended in 200 μL of complete NeuroCult™ medium (NeuroCult™ NS-A Basal Medium & NeuroCult™ Proliferation Supplements; StemCell Technologies Inc. with 20 ng/ml of EGF, 10 ng/mL basic fibroblast growth factor—bFGF and 2 μg/mL heparin) then mechanically dissociated using a disposable plastic pipette tip into a single cell suspension and filtered through a 40 μm nylon cell strainer (Falcon). A cell count was performed using Trypan blue exclusion and cells were diluted to a concentration of $2.17 \times 10^5$ cells per/mL in complete NeuroCult™ medium (NeuroCult™ NS-A Basal Medium & NeuroCult™ Proliferation Supplements; StemCell Technologies Inc. with 20 ng/ml of EGF, 10 ng/mL basic fibroblast growth factor—bFGF and 2 μg/mL heparin).

A 3.3 ml solution of the semi-solid NSC assay media was obtained by adding the following components in the given order:

| | |
|---|---|
| NeuroCult ™ NCFC serum-free medium without cytokines (StemCell Technologies) | 1700 μl |
| NeuroCult ™ Proliferation Supplements (StemCell Technologies) | 330 μl |
| Epidermal Growth Factor (10 μg/ml) | 6.6 μl |
| Basic Fibroblast Growth Factor (10 μg/ml) | 3.3 μl |
| Heparin Solution (0.2%) | 6.6 μl |
| Human Cells ($2.17 \times 10^5$ cell/ml) | 25 μl |
| Collagen (Bovine, StemCell Technologies) | 1300 μl |
| Total Volume | 3361 μl |

The resulting solution was mixed well to evenly distribute the cells throughout the medium. 1.5 ml of the suspension was plated into individual 35 mm tissue culture plates at a final density of 7500 cells per dish. Cultures are placed in a tissue culture incubator set at 37° C. 100% humidity and 5% $CO_2$. The colonies are enumerated and sized number between day 14-28 (FIG. 26).

Example 22

Different NCFC Colony Sizes Generated by Fetal Human Cortical Cells

Single cell suspensions of fetal human neurospheres were cultured in the NCFC assay as detailed in Example 21 above. By 21-28 days, colonies can be classified into at least 4 categories: 1) greater than 2 mm in diameter (FIG. 26A), 2) 1-2 mm in diameter (FIG. 26B), 3) 0.5-1 mm in diameter (FIG. 26C), and 4) less than 0.5 mm in diameter (FIG. 26D). FIG. 26 shows the different colony sizes derived from single cell suspension of human cortical cells cultured in the NCFC assay. The morphology of the colonies generated by fetal human cortical cells in the NCFC assay differs from the colonies generated by mouse (FIG. 7) and rat cells (FIG. 23). The cells within the different sized colonies are more dispersed and fewer cells are seen in the colonies >2 mm and 1-2 mm in diameters.

Example 23

Neural Colony Forming Cell (NCFC) Assay Using Different Growth Factors

The presence of subpopulations of EGF, FGF and EGF plus FGF-responsive stem and progenitor cells thought to exist in the embryonic and adult mouse CNS was measured using the NCFC assay. Striata were dissected from Embryonic Day 14 $CD_1$ albino mouse embryos (Charles River) using standard microdissection techniques. Tissue is collected in phosphate-buffered saline with 2% glucose then mechanically dissociated using a fire-polished glass pipette into a single cell suspension, washed once and filtered through a 40 μm nylon cell strainer (Falcon) and diluted to a concentration of $6.51 \times 10^5$ cells per/mL in complete NeuroCult™ medium (NeuroCult™ Basal Medium & NeuroCult™ Proliferation Supplements; StemCell Technologies Inc. with 20 ng/ml of EGF). A 3.3 ml solution of the semi-solid NSC assay media was made up with the components listed below with the exception that the individual growth factors were added either alone or in combination:

| | |
|---|---|
| NeuroCult NCFC serum-free medium without cytokines (StemCell Technologies) | 1700 μl |
| NeuroCult ™ Proliferation Supplements (StemCell Technologies) | 330 μl |
| Epidermal Growth Factor (10 μg/ml) | 6.6 μl |
| OR Basic Fibroblast Growth Factor (10 μg/ml) | 3.3 μl |
| Heparin solution (0.2%) - added with bFGF only | 6.6 μl |
| Cells ($6.51 \times 10^5$ cell/ml) | 25 μl |
| Collagen (Bovine, StemCell Technologies) - ADDED LAST | 1300 μl |
| Total Volume | 3361 μl |

The resulting solution is mixed well to evenly distribute the cells throughout the medium. 1.5 ml of the suspension is plated into individual 35 mm tissue culture plates at a final density of 7500 cells per dish. Cultures are placed in a tissue culture incubator set at 37° C. 100% humidity and 5% $CO_2$. The EGF, FGF and EGF+FGF colonies were enumerated and sized between day 14-28.

Example 24

Frequency of Colonies of the Various Sizes Generated by E14 Primary Mouse Striatal Cells in the NCFC Assay Containing Different Growth Factors The NCFC assay was performed using E14 primary mouse striatal cells according to procedure outlined in Example 23 with the growth factors, EGF, bFGF and EGF plus bFGF. The growth factor-responsive cells which formed colonies can be sized and counted and the frequency of colonies within each of these size categories graphed per total cells plated (FIG. 27). In the presence of EGF, FGF or EGF plus FGF, the frequency of colonies less than 0.5 mm in size is highest with a very small fraction (<0.1%) forming large colonies greater than 2 mm in diameter. The results indicated that in the presence of EGF and FGF, more colonies are obtained however most of the colonies are <0.5 mm and derived from progenitor cells as determined by the functional assays performed on the cells within these colonies.

Example 25

In situ Immunostaining of NCFC Colonies Overlaid with Serum with Markers Specific for Differentiated Primary E14 Mouse Striatal Cells The colonies formed in the NCFC assay can also be overlaid with serum to induce cells within the different colonies to differentiate into the mature neural lineages and then immunocytochemically stained directly in situ. Primary E14 mouse striatal cells were cultured in the NCFC assay according to the procedure outlined in Example 12 for 21 days. At the end of the culture period, 1 mL of NeuroCult™ complete media (StemCell Technologies Inc.) containing 1% fetal bovine serum was overlaid on top each NCFC dish and incubated for 10 days. In situ dehydration, fixing and permeabilization of the collagen and embedded-colonies in the NCFC assay was then performed according to the procedure outlined in Example 11. The samples were then labeled with the primary antibody directed against Beta-Tubulin, a marker specific for immature and mature neurons. The anti-Beta-Tubulin antibody was diluted at 1:1000 in PBS containing 10% goat serum. Approximate 500 μL of the diluted antibody was then added directly onto the dehydrated collagen gel on the glass slide and a piece of parafilm was placed on top of the antibody solution. All samples were incubated for 2 hours at 37° C. After the incubation period, the primary antibody was washed off with three 5-minute washes using PBS. Next, the secondary antibody, goat anti-mouse IgG (H+L) Texas Red-conjugated was diluted in PBS containing 2% goat serum, and added directly to the dehydrated collagen gel on the to glass slide. A piece of parafilm was placed on top of the antibody solution and the samples were incubated with the secondary antibodies for 30 minutes at 37° C. After the incubation, the secondary antibodies were washed off with three 5-minute washes using PBS. 5 μL of mounting medium was added in the middle of the each dehydrated collagen gel and then covered with a coverslip avoiding trapping any air bubbles. The immunfluorescence was visualized under a fluorescent microscope using the appropriate filters for each fluorophore.

Few cells within colonies >2 mm expressed B-Tubulin (FIGS. 28A and B). Colonies 1-2 mm (FIGS. 28C and D), 0.5 -1 mm in diameter (FIG. 28D) and <0.5 mm in diameter (FIG. 28E) contained higher numbers of cells which were positive for B-Tubulin expression compared to cells within colonies >2 mm in diameter. This procedure allows the detection of differentiated cells within the NCFC colonies after exposure to serum.

Example 26

Use of Methycellulose and Primary E14 Mouse Striatal in the NCFC Assay

The semi-solid medium used in the NCFC assay described above is collagen. Other types of semi-solid medium such as methycellulose, can also be used to generate neural colonies from single cell suspensions. The ability of neural cells isolated from mouse CNS tissue to form colonies in a methycellulose-based semi-solid medium was compared to collagen-based medium (Example 1).

Striata were dissected from Embryonic Day 14 $CD_1$ mouse embryos (Charles River) using standard microdissection techniques. Tissue is collected in phosphate-buffered saline with 2% glucose then mechanically dissociated using a fire-polished glass pipette into a single cell suspension, washed once and filtered through a 40 μm nylon cell strainer (Falcon) and diluted to a concentration of $6.51 \times 10^5$ cells per/mL in complete NeuroCult™ medium (NeuroCult™ Basal Medium & NeuroCult™ Proliferation Supplements; StemCell Technologies Inc. with 20 ng/ml of EGF). A 3.3 ml solution of the semi-solid collagen-based assay media was made by adding the following components in the given order:

| | |
|---|---|
| NeuroCult NCFC serum-free medium without cytokines (StemCell Technologies) | 1700 μl |
| NeuroCult ™ Proliferation Supplements (StemCell Technologies) | 330 μl |
| Epidermal Growth Factor (10 μg/ml) | 6.6 μl |
| Cells ($6.51 \times 10^5$ cells/ml) | 25 μl |
| Collagen (Bovine, StemCell Technologies) | 1300 μl |
| Total Volume | 3361 μl |

The resulting solution was mixed well to evenly distribute the cells throughout the medium. 1.5 ml of the suspension was plated into individual 35 mm tissue culture plates at a final density of 7500 cells per dish. Cultures were placed in a tissue culture incubator set at 37° C. 100% humidity and 5% $CO_2$. The colonies were enumerated and sized between day 14-28.

At the same time, a solution of the methycellulose-based assay media was made by adding the following components in the given order to give a 1% final concentration of methycellulose:

| | |
|---|---|
| NeuroCult NCFC serum-free medium without cytokines (StemCell Technologies) | 1700 μl |
| NeuroCult ™ Proliferation Supplements (StemCell Technolgies) | 330 μl |
| Epidermal Growth Factor (10 μg/ml) | 6.6 μl |
| Cells ($6.51 \times 10^5$ cells/ml) | 25 μl |
| Methycellulose (StemCell Technologies) | 1300 μl |
| Total Volume | 3361 μl |

The resulting solution was mixed well to evenly distribute the cells throughout the medium. 1.5 ml of the suspension was plated using a blunt-ended needle into individual 35 mm tissue culture plates at a final density of 7500 cells per dish. Cultures were placed in a tissue culture incubator set at 37° C. 100% humidity and 5% $CO_2$. The colonies were enumerated and number between day 14-28. FIG. 29 shows 3 individual colonies less than 0.5 mm in diameter, which were generated by E14 striatal mouse cells.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

The relative frequency of colonies within each of the four size categories in NCFC Assay.

| Colony Size | NCFC frequency (%) mean ± SD |
|---|---|
| >2 mm | 0.09 ± 0.03 |
| 1-2 mm | 0.11 ± 0.04 |
| 0.5-1 mm | 0.12 ± 0.11 |
| <0.5 mm | 0.38 ± 0.21 |
| Total colonies (range) | 0.52-1.1 |

Single cell suspensions from primary embryonic mouse striata were plated at a low density in serum-free semi-solid media containing EGF. Clonally-derived colonies were assigned to four size categories after 21 days in culture. The NCFC frequency (%) relative to total number of cells plated was calculated by NCFC frequency (%)=(number of colonies/total cells plated)×100. Between 0.52-1.1% of the total cells plated proliferated to varying degrees and formed colonies. A very small fraction (0.09%) of the total cells plated formed large (>2 mm) colonies. The majority of the colonies formed were <1 mm (0.5%) suggesting a more limited proliferative potential.

References

Altman, J. (1962). Are new neurons formed in the brains of adult mammals? *Science* 135, 1127-1129.

Altman, J. & Das, G. D. Autoradiographic and histological studies of postnatal neurogenesis. I. A longitudinal investigation of the kinetics, migration and transformation of cells incorporating tritiated thymidine in neonate rats, with special reference to postnatal neurogenesis in some brain regions. *J. Comp. Neurol.* 126, 337-390(1966).

Alvarez-Buylla A, Garcia-Verdugo J M, Tramontin A D (2001) A unified hypothesis on the lineage of neural stem cells. *Nat Rev Neurosci* 2:287-293.

Morshead C M, Reynolds B A, Craig C G, McBumey M W, Staines W A, Morassutti D, Weiss S, van der Kooy D (1994) Neural stem cells in the adult mammalian forebrain: a relatively quiescent subpopulation of subependymal cells. *Neuron* 13:1071-1082.

Potten, C. S., and Loeffler, M. (1990). Stem cells: Attributes, cycles, spirals, pitfalls and uncertainties. Lessons for and from the Crypt. *Development* 110, 1001-1020.

Reynolds B A, Weiss S (1992) Generation of neurons and astrocytes from isolated cells of the adult mammalian central nervous system. *Science* 225:1707-1710.

Reynolds B A, Weiss S (1996) Clonal and population analyses demonstrate that an EGF-responsive mammalian embryonic CNS precursor is a stem cell. *Dev Biol* 175:1-13.

Shimazaki T, Shingo T, Weiss S (2001) The ciliary neurotrophic factor/leukemia inhibitory factor/gp130 receptor complex operates in the maintenance of mammalian forebrain neural stem cells. *J Neurosci* 21:7642-7653.

The invention claimed is:

1. A method for identifying neural stem cells or neural progenitor cells comprising:
    (a) suspending neural cells in a semi-solid medium which supports the growth of neural cells;
    (b) plating the cells in the semi-solid medium at a cell density that allows for the production of colonies;

(c) culturing the plated cells until size differences can be discerned between the colonies;
(d) estimating colony size; and
(e) identiying neural stem cells or neural progenitor cells based on the colony size wherein the larger colonies are produced by neural stem cells and wherein the smaller colonies are produced by neural progenitor cells.

2. A method according claim 1 wherein the neural cells are mammalian.

3. A method according to claim 2 wherein the neural cells are from human, rat or mouse.

4. A method according to claim 1 wherein the neural cells are from primary CNS tissue or cultured neurospheres.

5. A method according to claim 1 wherein the semi-solid medium is collagen based.

6. A method according to claim 1 wherein the semi-solid medium is methylcellulose based.

7. A method according to claim 1 wherein the neural cells are diluted in a culture medium prior to step (a).

8. A method according to claim 7 wherein epidermal growth factor (EGF) is added to the medium.

9. A method according to claim 7 wherein basic fibroblast growth factor (bFGF) is added to the medium.

10. A method according to claim 9 wherein the culture medium is serum free.

11. A method according to clam 1 wherein the cells are plated in step (b) at a density of about 1000 to 25,000 cells per 35 mm culture dish.

12. A method according to clam 1 wherein the cells are cultured in step (c) for about 10 to about 28 days.

13. A method according to claim 1 wherein in step (d) a colony size of greater than 2.0 mm indicates neural stem cells.

14. A method according to claim 1 wherein in step (d) a colony size of less than or equal to 2.0 mm indicates neural progenitor cells.

* * * * *